United States Patent
Blake

(10) Patent No.: US 9,751,102 B2
(45) Date of Patent: Sep. 5, 2017

(54) METHOD FOR DISPENSING A PRODUCT FROM A CONTAINER

(71) Applicant: ALTERNATIVE PACKAGING SOLUTIONS, LLC, New York, NY (US)

(72) Inventor: William Sydney Blake, Linwood, NJ (US)

(73) Assignee: Alternative Packaging Solutions LLC, New York, NY (US)

( * ) Notice: Subject to any disclaimer, the term of this patent is extended or adjusted under 35 U.S.C. 154(b) by 0 days.

(21) Appl. No.: 15/231,994

(22) Filed: Aug. 9, 2016

(65) Prior Publication Data
US 2016/0354794 A1    Dec. 8, 2016

Related U.S. Application Data

(63) Continuation of application No. 14/225,146, filed on Mar. 25, 2014, now Pat. No. 9,415,401, which is a
(Continued)

(51) Int. Cl.
| | |
|---|---|
| *B05B 11/00* | (2006.01) |
| *B05B 1/00* | (2006.01) |
| *F04B 35/01* | (2006.01) |
| *F04B 39/00* | (2006.01) |
| *F04B 39/08* | (2006.01) |

(Continued)

(52) U.S. Cl.
CPC ............ *B05B 11/3015* (2013.01); *B05B 1/00* (2013.01); *B05B 11/3047* (2013.01); *B05B 11/3074* (2013.01); *F04B 35/01* (2013.01); *F04B 39/0005* (2013.01); *F04B 39/08* (2013.01); *F04B 39/12* (2013.01); *F04B 39/121* (2013.01); *F04B 39/123* (2013.01); *F04B 41/02* (2013.01)

(58) Field of Classification Search
CPC ............ B05B 11/3015; B05B 11/3047; B05B 11/3074; B05B 1/00; F04B 41/02; F04B 39/12; F04B 39/121; F04B 39/123; F04B 35/01; F04B 39/0005; F04B 39/08
USPC ........................................................ 222/1
See application file for complete search history.

(56) References Cited

U.S. PATENT DOCUMENTS

| | | |
|---|---|---|
| 3,104,785 A | 9/1963 | Beard, Jr. |
| 3,746,261 A | 7/1973 | Nozawa et al. |
| | (Continued) | |

FOREIGN PATENT DOCUMENTS

JP    H06-27650 U    4/1994

OTHER PUBLICATIONS

Machine-generated English language translation of JP H06-27650 obtained from the European Patent Office.

*Primary Examiner* — Donnell Long
(74) *Attorney, Agent, or Firm* — Rankin, Hill & Clark LLP

(57) ABSTRACT

A method for dispensing a product from an interior volume of a container to which a power assembly is secured, which includes rotating an actuator sleeve of the power assembly in one direction relative to the container to draw an amount of the product from the interior volume into a pump chamber and to pressurize the pump chamber, and temporarily depressing an actuator of the power assembly to dispense a portion of the product from the pump chamber through a nozzle for a duration of time during which the actuator is temporarily depressed. During the duration when the product is dispensed from the container, the power assembly does not rotate relative to the container, and the power assembly is never rotated in an opposite direction.

10 Claims, 40 Drawing Sheets

Related U.S. Application Data continuation of application No. 13/439,510, filed on Apr. 4, 2012, now Pat. No. 8,720,746.

(51) Int. Cl.
 *F04B 39/12* (2006.01)
 *F04B 41/02* (2006.01)

(56) References Cited

U.S. PATENT DOCUMENTS

| | | | |
|---|---|---|---|
| 3,777,945 A | 12/1973 | Nozawa et al. |
| 3,790,034 A | 2/1974 | Horvath |
| 3,792,800 A | 2/1974 | Capra et al. |
| 3,797,748 A | 3/1974 | Nozawa et al. |
| 3,799,448 A | 3/1974 | Nozawa et al. |
| 3,908,870 A | 9/1975 | Nozawa et al. |
| 3,940,029 A | 2/1976 | Horvath |
| 4,057,176 A | 11/1977 | Horvath |
| 4,105,145 A | 8/1978 | Capra |
| 4,147,280 A | 4/1979 | Spatz |
| 4,155,485 A | 5/1979 | Spatz |
| 4,167,941 A | 9/1979 | Capra et al. |
| 4,174,052 A | 11/1979 | Capra et al. |
| 4,174,055 A | 11/1979 | Capra et al. |
| 4,176,764 A | 12/1979 | Capra et al. |
| 4,192,442 A | 3/1980 | Bastian et al. |
| 4,220,264 A | 9/1980 | Gamadia |
| 4,222,500 A | 9/1980 | Capra et al. |
| 4,222,501 A | 9/1980 | Hammett et al. |
| 4,235,353 A | 11/1980 | Capra et al. |
| 4,241,853 A | 12/1980 | Pauls et al. |
| 4,243,159 A | 1/1981 | Spatz |
| 4,260,082 A | 4/1981 | Rooney et al. |
| 4,387,833 A | 6/1983 | Venus, Jr. |
| 4,423,829 A | 1/1984 | Katz |
| 4,474,215 A | 10/1984 | Richter et al. |
| 4,485,943 A | 12/1984 | Czech |
| 4,564,130 A | 1/1986 | Eulenburg |
| 4,607,762 A | 8/1986 | Zulauf et al. |
| 4,858,788 A | 8/1989 | Meckenstock |
| 4,872,595 A | 10/1989 | Hammett et al. |
| 4,892,232 A | 1/1990 | Martin |
| 5,183,185 A | 2/1993 | Hutcheson et al. |
| 5,240,153 A | 8/1993 | Tubaki et al. |
| 5,328,062 A | 7/1994 | Tubaki et al. |
| 5,392,959 A | 2/1995 | Tubaki et al. |
| 5,405,060 A | 4/1995 | von Schuckmann |
| 5,474,215 A | 12/1995 | Tubaki et al. |
| 5,549,223 A | 8/1996 | Hori |
| 5,855,322 A | 1/1999 | Py |
| 5,857,595 A | 1/1999 | Nilson |
| 6,053,433 A | 4/2000 | Py |
| 6,059,151 A | 5/2000 | Fuchs |
| 6,109,479 A | 8/2000 | Ruckseschel |
| 6,543,703 B2 | 4/2003 | Blake |
| 6,609,666 B1 | 8/2003 | Blake |
| 6,708,852 B2 | 3/2004 | Blake |
| 6,793,100 B2 | 9/2004 | Iizuka et al. |
| 7,066,359 B2 | 6/2006 | Greiner-Perth |
| 7,845,521 B2 | 12/2010 | Blake |
| 8,177,101 B1 | 5/2012 | Blake |
| 8,286,837 B1 | 10/2012 | Blake |
| 2002/0030069 A1 | 3/2002 | Auer |
| 2011/0303702 A1 | 12/2011 | Wang |
| 2012/0292344 A1 | 11/2012 | Bertin et al. |

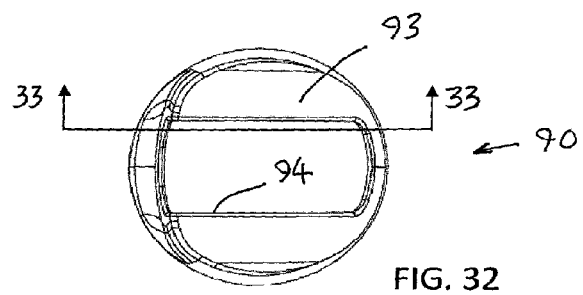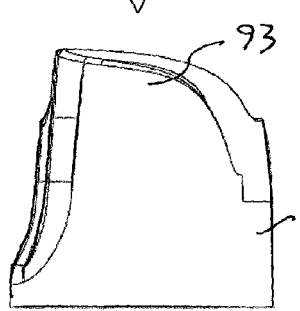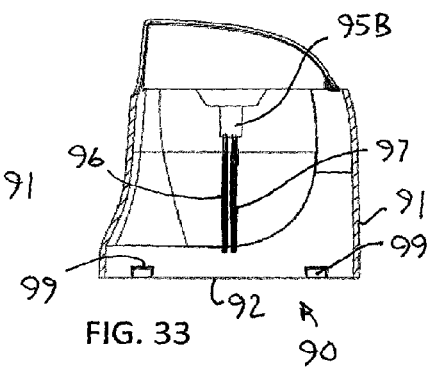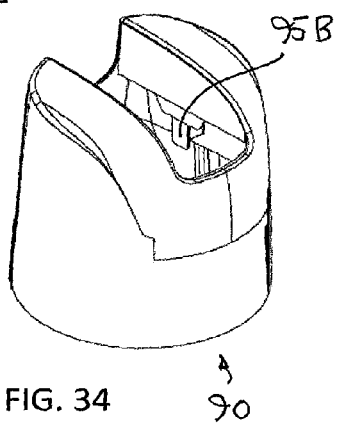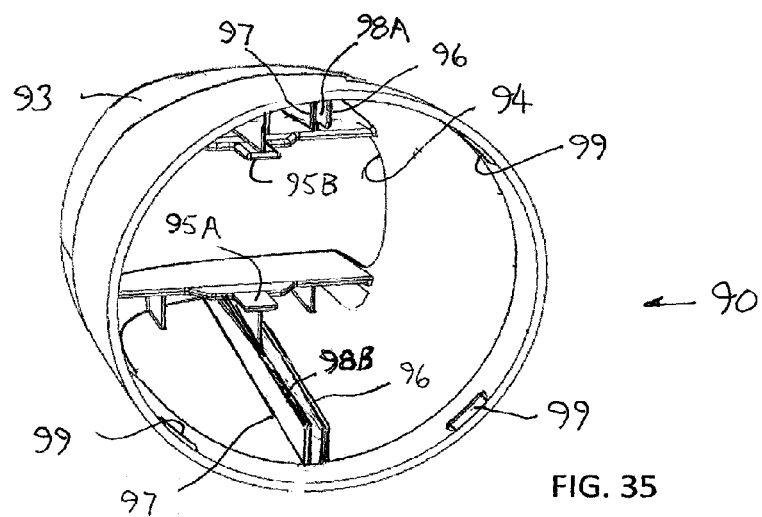

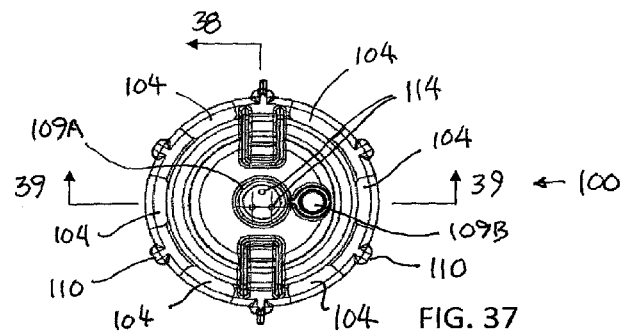
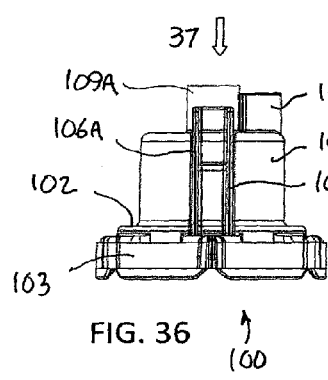
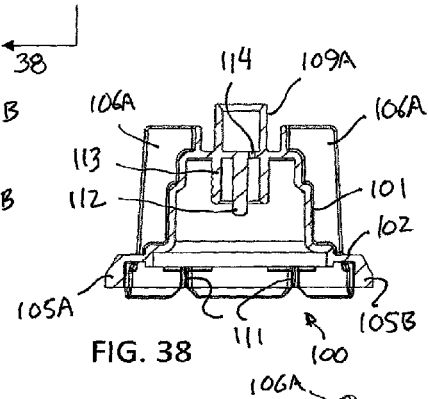
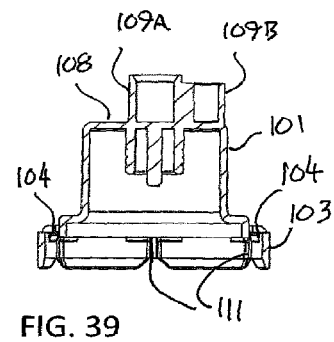
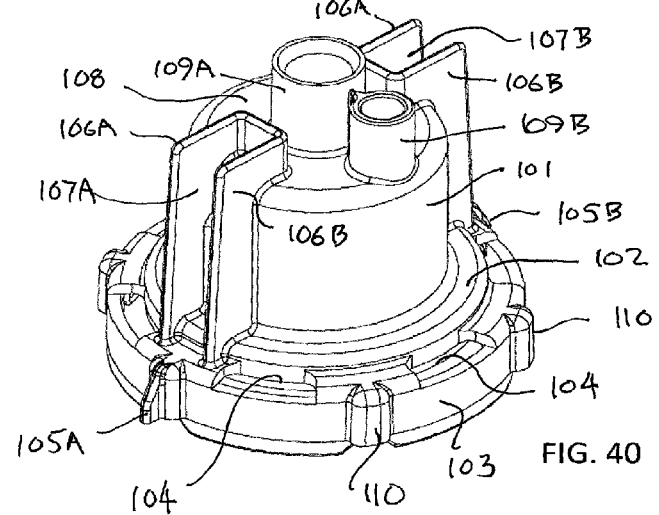

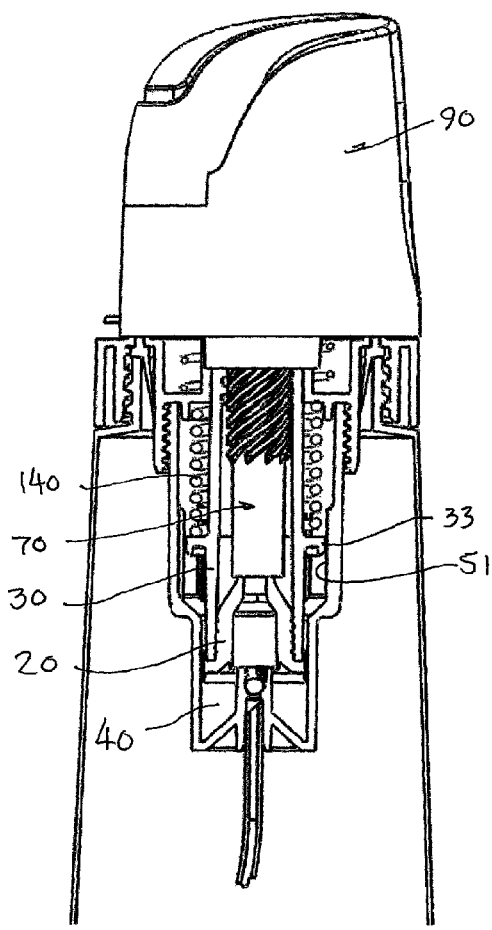
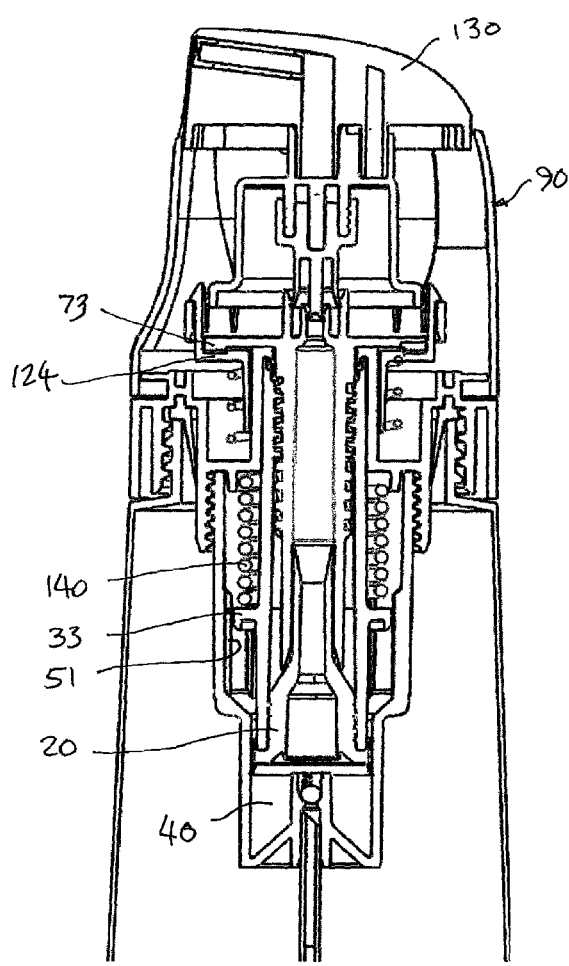
FIG. 52
FIG. 53

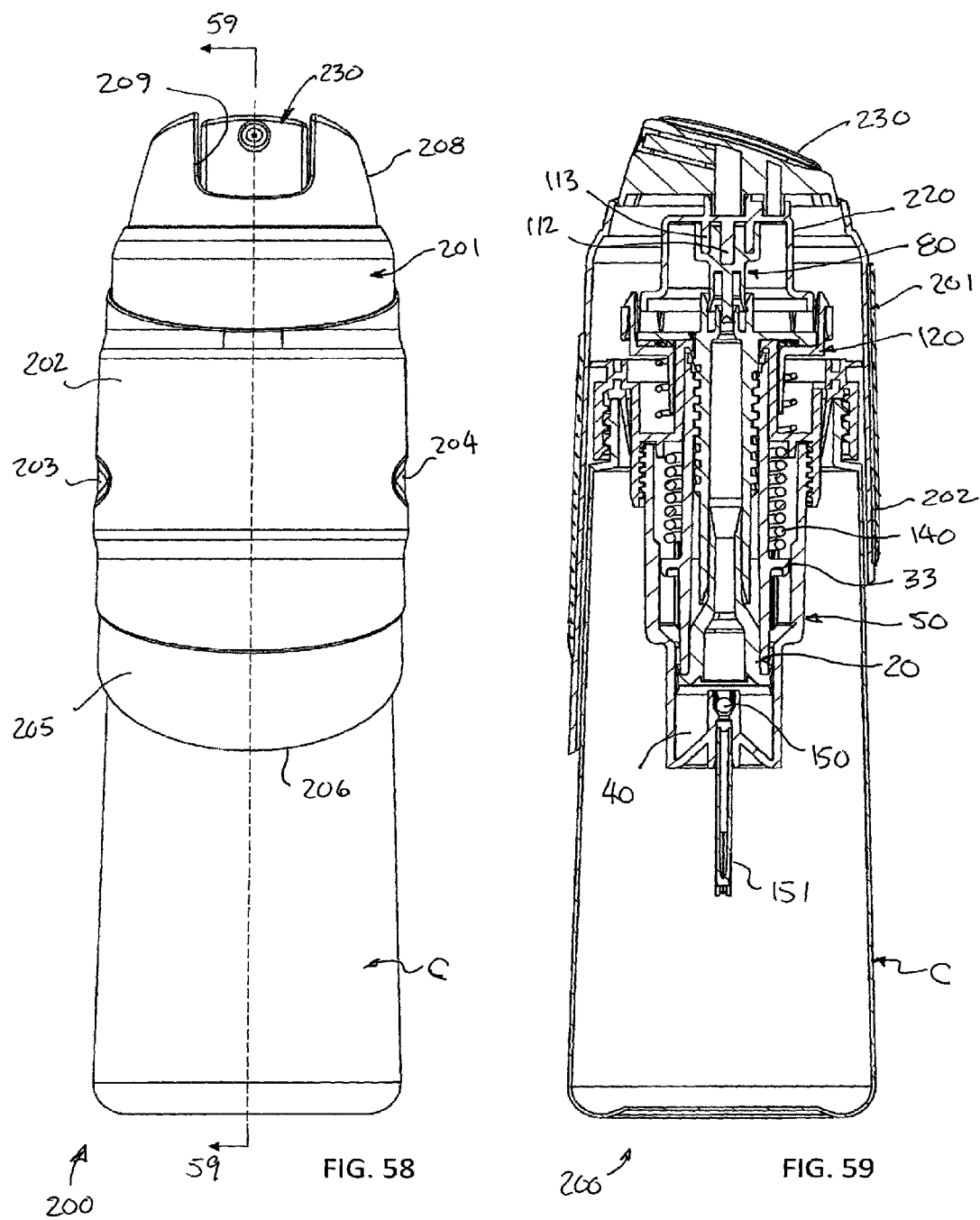

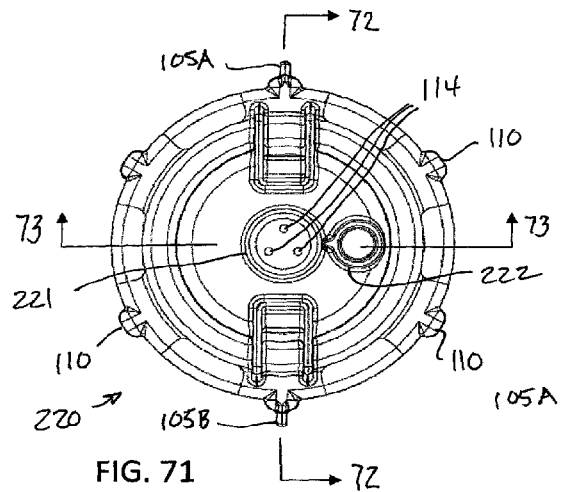
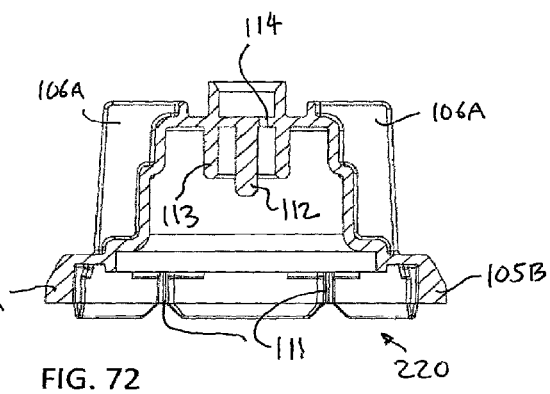
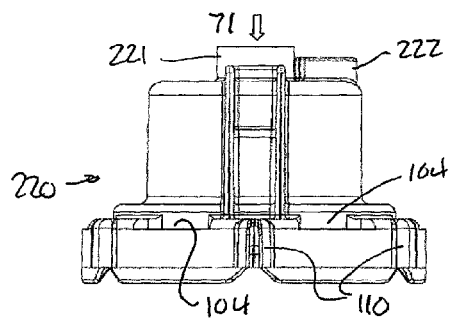
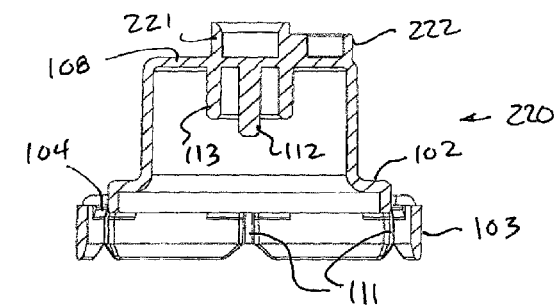
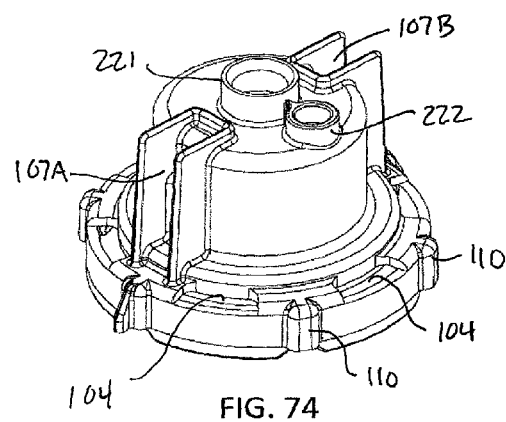
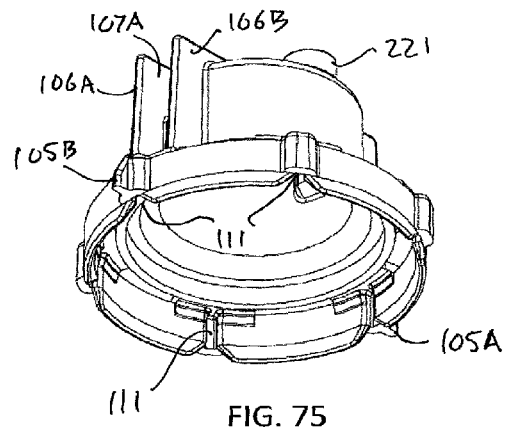

METHOD FOR DISPENSING A PRODUCT FROM A CONTAINER

This application is a continuation of U.S. application Ser. No. 14/225,146, filed Mar. 25, 2014, now U.S. Pat. No. 9,415,401, which is a continuation of U.S. application Ser. No. 13/439,510, filed Apr. 4, 2012, now U.S. Pat. No. 8,720,746.

TECHNICAL FIELD

The present invention relates to a method for dispensing a product from a container, specifically to a method for dispensing a product from a container that is energized mechanically and pressurized by a non-chemical means.

BACKGROUND ART

Both chemically driven and mechanically operated spray dispensers have been in use for many years and are still popular due to their convenience. However, aerosol dispensers that use chemical propellants have come under increasing scrutiny and restrictions are being imposed upon them due to their adverse impact upon the environment as well as the hazards associated with handling them and related insurance issues. Also, conventional non-chemical mechanical spray dispensers are typically unfavorably compared with chemically driven aerosols because they are bulky and commonly require multiple steps in their operation, making them difficult to operate, especially by persons suffering from diseases or disorders such as arthritis. They also require a large number of parts and a large amount of material to produce them, which due to the increasing cost of energy makes them prohibitively expensive to manufacture. This, in turn, makes them too costly for use at the lower price range of consumer products. Moreover, there is a general reluctance to change from the pressurized propellant-driven aerosol systems including bag in a can or piston in a can devices.

Some mechanically operated aerosol devices incorporate storage chambers that require a step in which a metered amount of product must first be obtained and then transferred into a power chamber that provides the pressure for dispensing the product over a certain duration. These types of devices are energy inefficient and degrade over time and or usage, as well as being too costly due to their exotic material structure and dynamic nature for use with a range of desirable products that currently use finger pumps or chemical aerosol valves. Bag in a can devices are complex systems that do not have all the attributes of chemical aerosol delivery.

By way of example, U.S. Pat. Nos. 4,387,833 and 4,423,829 exhibit some of the above shortcomings.

U.S. Pat. No. 4,147,280 to Spatz requires dual separate helixes and a cap for unusual manipulation to deliver product as a spray. U.S. Pat. Nos. 4,167,041, 4,174,052, 4,174,055, and 4,222,500 to Capra et. al., U.S. Pat. No. 4,872,595 to Ilammet et. al., U.S. Pat. No. 5,183,185 to Ilutcheson et. al. and U.S. Pat. No. 6,708,852 to Blake all require a storage chamber. In addition, Blake requires multiple actions to set up.

Other patents for reference are U.S. Pat. Nos. 4,423,829 and 4,387,833 that may be of interest. All have drawbacks in expense for commercial acceptance and feasibility if mass produced at high levels in existing market applications.

Despite the efforts of such devices as shown in the forgoing patents, there remains a need for a more convenient to use, less expensive, and compact mechanically energized duration spray mechanism that performs to dispense product comparably to the chemically energized dispensers in common use. Specifically, it would be desirable to have a one turn actuated duration spray pump delivery system that is free of the disadvantages seen in conventional chemical and mechanically energized aerosol dispensers.

SUMMARY OF THE DISCLOSURE

The present invention is a duration spray dispenser that, among a variety of features, does not rely upon chemical propellants for its operation, that eliminates the need for the charging chamber technology used in conventional mechanically operated aerosol dispensers, that reduces the multiple steps required to operate conventional delivery systems, that is close in convenience to chemically energized dispenser systems, and/or that has a size comparable to that of conventional finger- and trigger-actuated pumps.

The mechanically actuated dispenser of the invention provides a neck or neck finish with a grippable portion(s), including for products that currently utilize finger pumps, and has a number of parts comparable to the number of parts in single stroke pumps. It also provides longer duration sprays than conventional mechanically energized dispensers.

The duration spray dispenser of the invention comprises a power assembly that can be attached to a container of product to obtain a duration discharge of the product upon a single turn or partial turn of an actuator to pressurize product and ready it for dispensing. The power assembly can be used with various energy storage means such as springs, gases or elastics to exert pressure on product to be dispensed when the actuator is turned.

The power assembly comprises a rotatable actuator sleeve connected through a drive means with a piston so that rotation of the actuator sleeve causes the piston to reciprocate in a first direction to draw product from the container and into a pump chamber. Reciprocation of the piston in the first direction stores energy in an energy storage means that acts on the piston to bias it in a second direction opposite to the first direction to pressurize the product in the pump chamber. A stem valve has a normally closed position that blocks discharge of product from the pump chamber, and an open position permitting discharge of product. A reciprocal actuator is connected with the stem valve to move it to its open position when the actuator is depressed. As product is depleted from the pump chamber the energy storage means pushes the piston back to an at-rest position to ready it for another dispensing cycle. An escapement mechanism connected in the drive means also is operated by depression of the actuator to disengage the drive means so that movement of the piston in the second direction does not cause movement of the actuator sleeve.

The drive means comprises a clutch disc connected to be rotated by rotation of the actuator sleeve, a drive screw connected with the clutch disc through interengaged gear teeth so that the drive screw is rotated by the clutch disc, and a piston housing connected to be reciprocated when the drive screw is rotated. The piston is carried by the piston housing for reciprocation in a cylinder cup, and with the cylinder cup defines the pump chamber.

The escapement mechanism includes the clutch disc, the interengaged gear teeth between the clutch disc and the drive screw, and the actuator. When the actuator is depressed it reciprocates the clutch disc away from the drive screw and disengages the gear teeth.

Interengaged helical threads between the drive screw and piston housing, and axial grooves and splines between the exterior of the piston housing and the cylinder cup, cause the piston housing and piston to reciprocate from a first, at-rest position to a second position to draw product from the container and into the pump chamber when the actuator sleeve is rotated. This motion of the piston also stores energy in the energy storage means that exerts pressure on the product drawn into the pump chamber. In the particular example disclosed herein, a full charge of the product to be dispensed can be drawn into the pump chamber by rotation of the actuator sleeve through only about 360°, but if desired the system can be designed to obtain a full charge of product to be dispensed when the actuator sleeve is rotated through a smaller angle, or through a larger angle if desired. Further, the actuator sleeve can be rotated through less than a full turn to obtain less than a full charge of product to be dispensed.

The energy storage component comprises a spring in the form of the dispenser and components thereof disclosed in this application, but it could alternatively comprise a pneumatic or elastic component and methods as disclosed in applicant's copending application Ser. Nos. 11/702,734 and 12/218,295, filed Feb. 6, 2007, and Jul. 14, 2008, respectively, the disclosures of which are incorporated in full herein by reference. Whichever type of energy storage device(s) is used, it preferably is pre-stressed or pre-compressed when the piston is in its at-rest position so that adequate pressure is exerted on the product in the pump chamber to obtain a suitable discharge of the product when the piston is at or near its arrest position.

The mechanically operated mechanisms of the present invention allow a consumer to make a single turn of an actuator sleeve and press down on a spray actuator to obtain a duration discharge of the product to be sprayed or dispensed. Moreover, after product has been drawn into the pump chamber the dispenser can be operated to dispense product in any orientation of the dispenser. Further, the mechanism described herein can be used with much smaller neck finishes, and the ratio of piston-to-cylinder diameters allow for easier actuation with much less force. These forces are comprised of only the friction that is encountered at the interface of the drive screw and piston housing and between the piston housing and cylinder cup as the piston moves along its predetermined path.

In the dispenser of the invention the escapement mechanism avoids "spin back" of the actuator sleeve that would otherwise result from the return movement of the piston under the influence of the driving force of the energy storage means during a dispensing cycle.

These new mechanisms can be used with standard spray actuators or actuators as depicted in U.S. Pat. Nos. 6,609,666 B1 and 6,543,703 B2, for example.

BRIEF DESCRIPTION OF THE DRAWINGS

The foregoing, as well as other objects and advantages of the invention, will become apparent from the following detailed description when taken in conjunction with the accompanying drawings, wherein like reference characters designate like parts throughout the several views, and wherein:

FIG. 31 is a side view in elevation of the actuator sleeve used in the mechanism of the invention.

FIG. 32 is an end view of the actuator sleeve, looking in the direction of arrow 32 in FIG. 31.

FIG. 33 is a view in section taken along line 33-33 in FIG. 32.

FIG. 34 is a top rear isometric view of the actuator sleeve.

FIG. 35 is an enlarged bottom isometric view of the actuator sleeve.

FIG. 36 is a side view in elevation of the actuator socket used in the mechanism of the invention.

FIG. 37 is an end view of the actuator socket, looking in the direction of arrow 36 in FIG. 35.

FIG. 38 is a sectional view taken along line 38-38 in FIG. 37.

FIG. 39 is a sectional view taken along line 39-39 in FIG. 37.

FIG. 40 is an enlarged top isometric view of the actuator socket.

FIG. 52 is a fragmentary sectional view of the mechanism in the state it is in with the actuator sleeve turned approximately one-half revolution.

FIG. 53 is a fragmentary sectional view of the mechanism in the state it is in when fully charged and ready to dispense product.

FIG. 58 is a front elevation view of a modified dispenser according to the disclosure, wherein the actuator sleeve has an over-molded cushioned sleeve and extends downwardly a greater distance over the upper end of the container.

FIG. 59 is a longitudinal view in section taken along line 59-59 in FIG. 58.

FIG. 70 is a side view in elevation of the actuator socket used in the assembly of FIGS. 58-62.

FIG. 71 is a top end view of the actuator socket, looking in the direction of the arrow 71 in FIG. 70.

FIG. 72 is a longitudinal sectional view taken along line 72-72 in FIG. 71.

FIG. 73 is a longitudinal sectional view taken along line 73-73 in FIG. 71.

FIG. 74 is a top isometric view of the actuator socket.

FIG. 75 is a bottom isometric view of the actuator socket.

DETAILED DESCRIPTION OF THE PREFERRED EMBODIMENTS OF THE INVENTION

Figure 1:
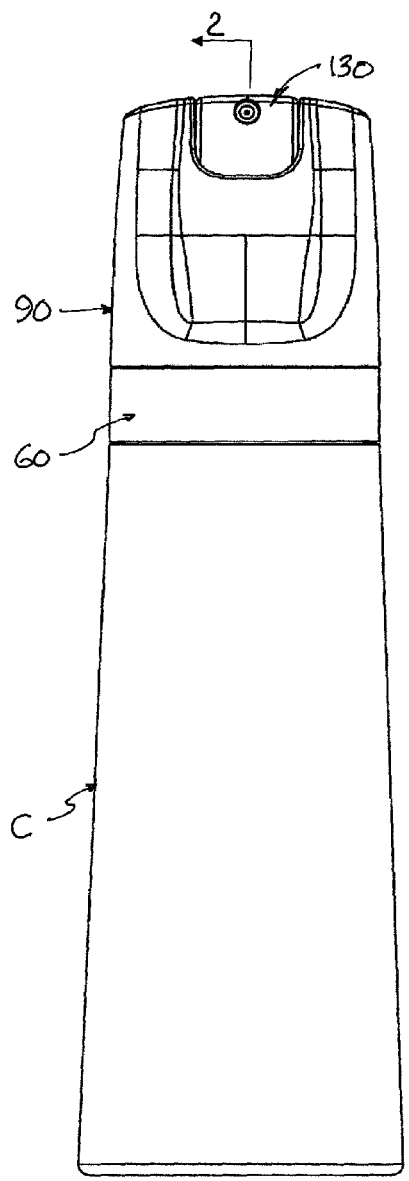
FIG. 1 is a front view in elevation of the dispenser described herein.
Figure 2:
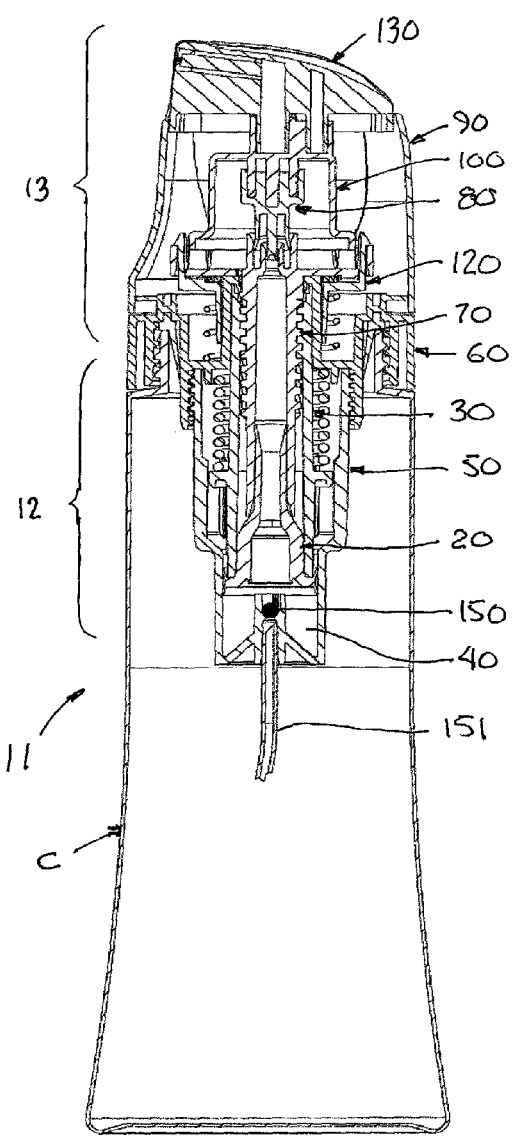
FIG. 2 is a slightly enlarged longitudinal sectional view taken along line 2-2 in FIG. 1, showing the pump and energy storage device in a compressed charged position ready to dispense product.
Figure 3:
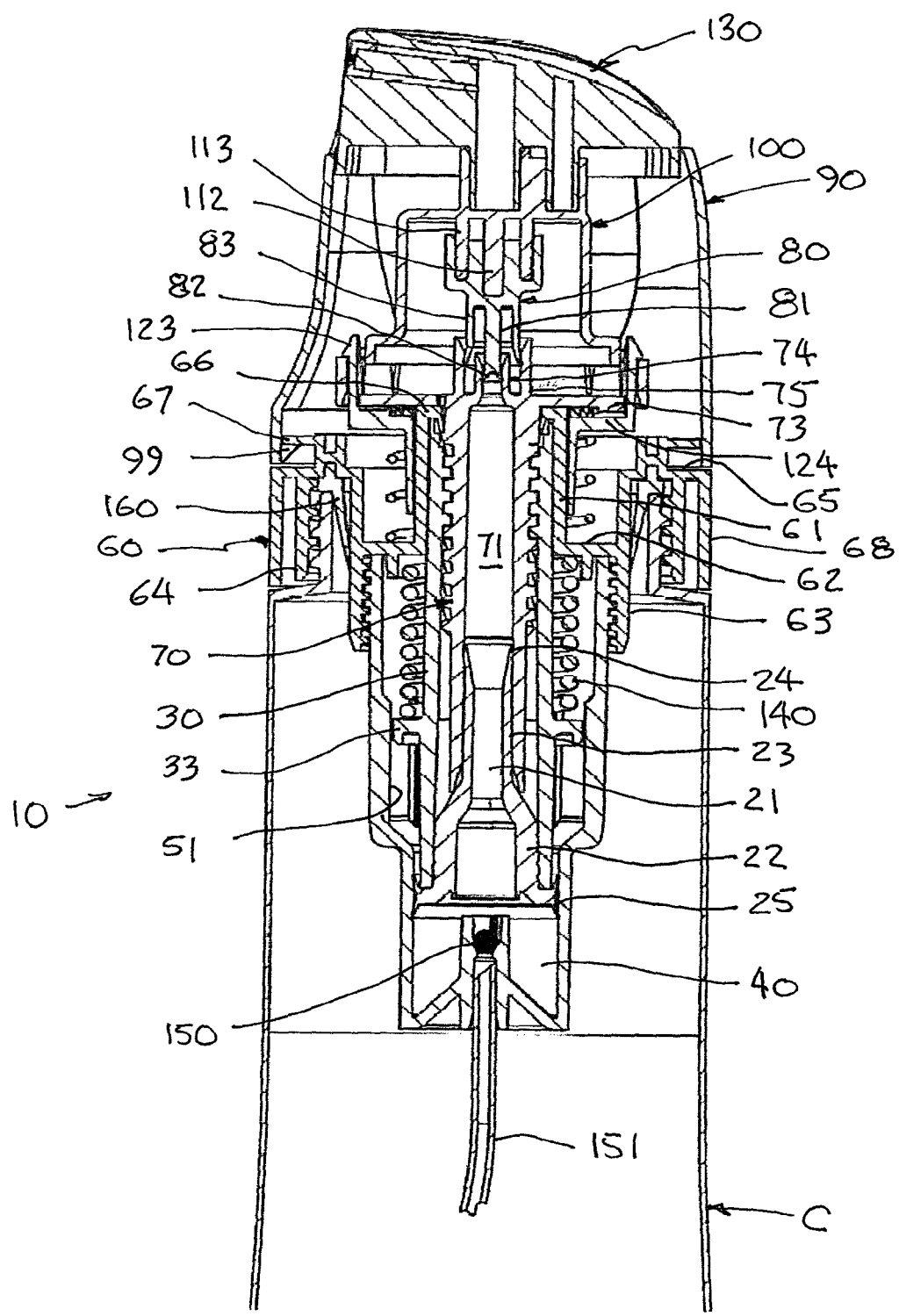
FIG. 3 is a further enlarged fragmentary view in section of the mechanism of FIG. 2.
Figure 4:
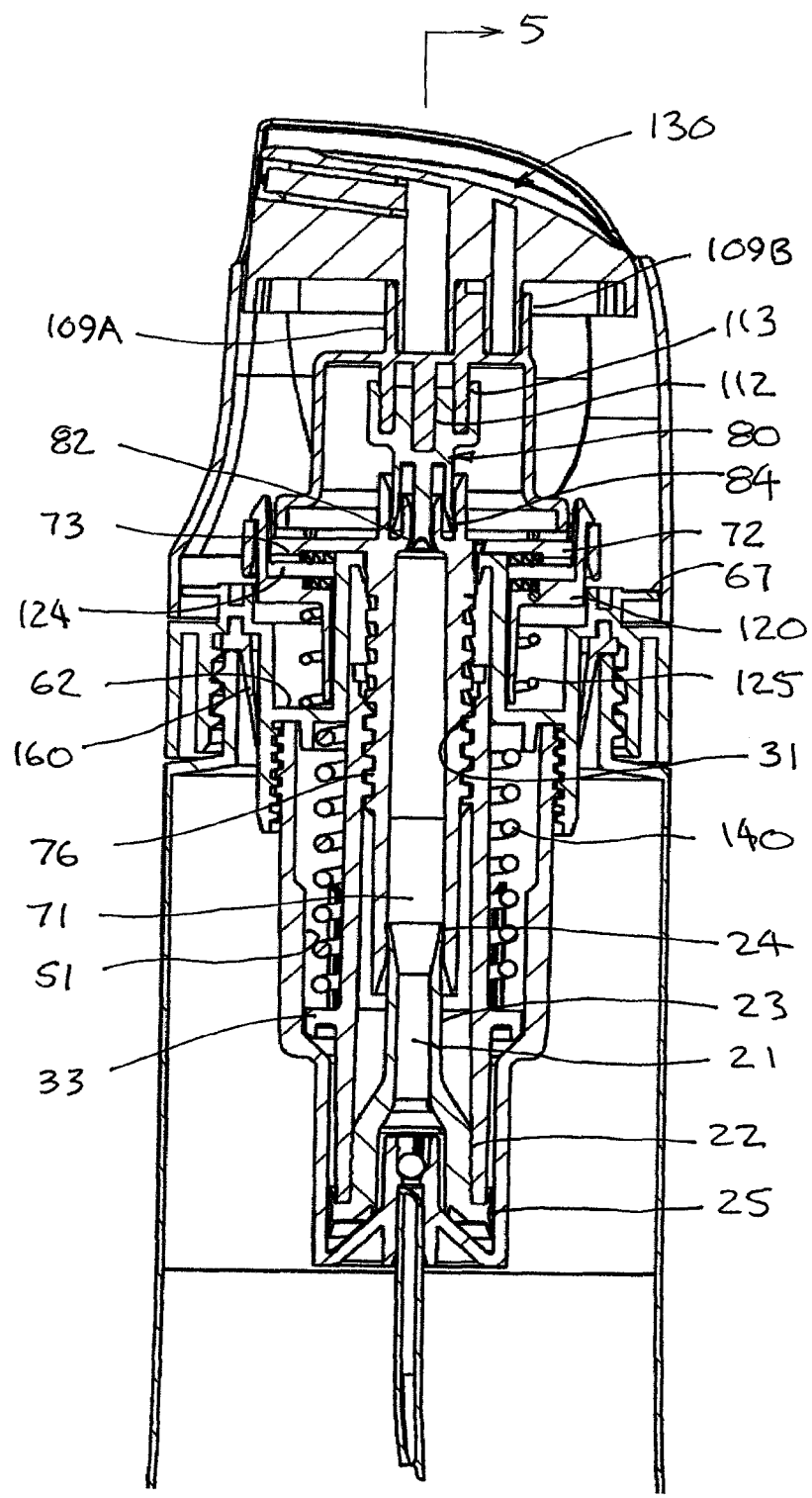
FIG. 4 is an enlarged sectional view similar to FIG. 3 but showing the mechanism with the actuator depressed and the stem valve open to dispense product, with the piston returned to its at rest position.
Figure 5:
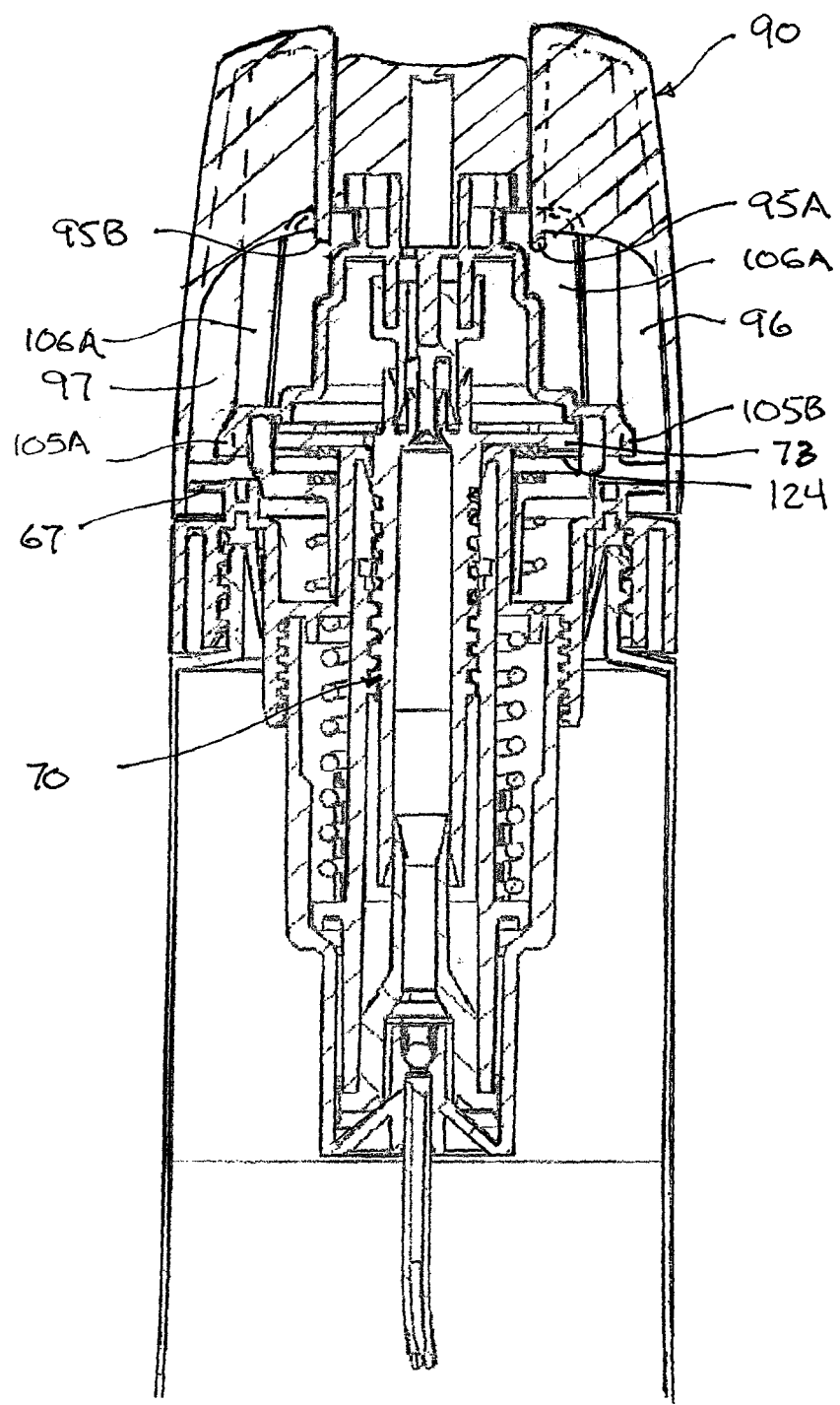
FIG. 5 is a fragmentary enlarged sectional view taken along line 5-5 in FIG. 4, showing engagement of the parts between the actuator sleeve and actuator socket that cause the actuator socket to rotate when the actuator sleeve is rotated.
Figure 6:
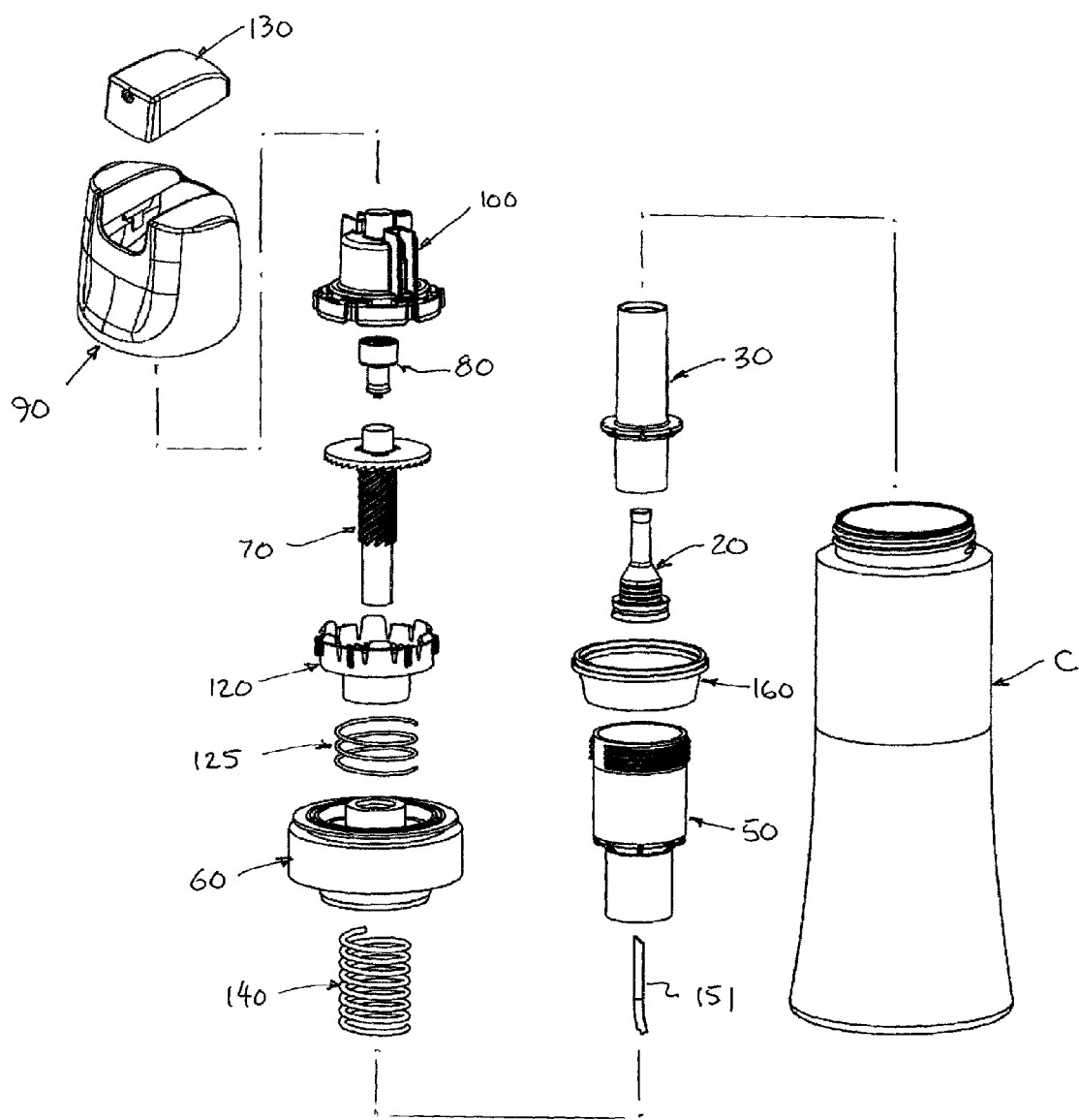
FIG. 6 is an exploded isometric view of the dispenser of FIGS. 1-5.
Figure 7:
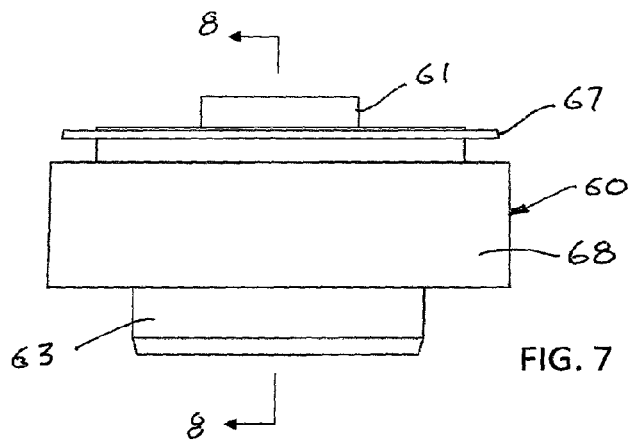
FIG. 7 is a side view in elevation of the container cap used in the assembly of FIGS. 1-5.
Figure 8:
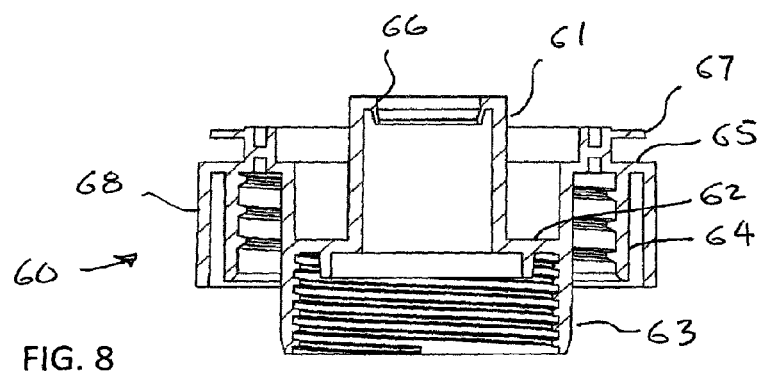
FIG. 8 is a sectional view taken along line 8-8 in FIG. 7.
Figure 9:
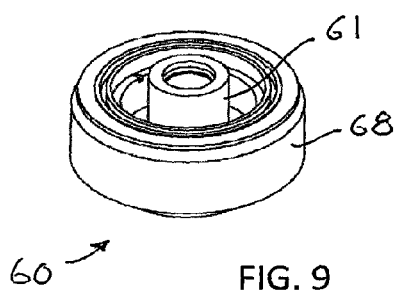
FIG. 9 is a top isometric view of the container cap of FIG. 7.
Figure 10:
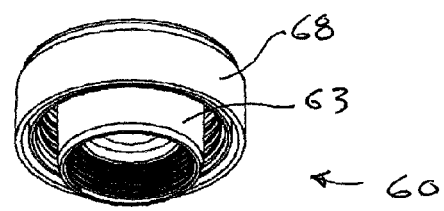
FIG. 10 is a bottom isometric view of the container cap.
Figure 11:
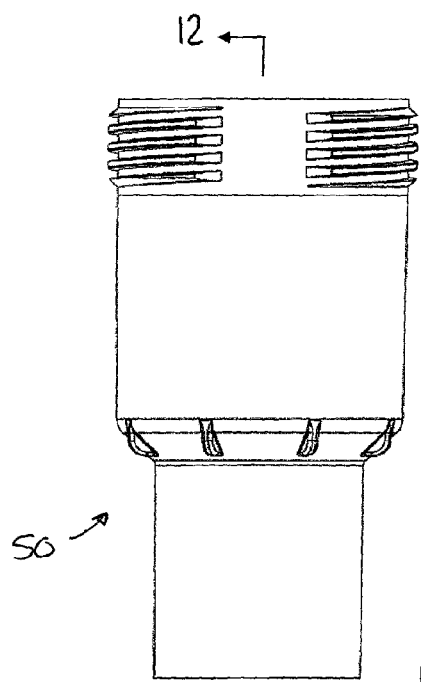
FIG. 11 is a side view in elevation of the piston cylinder cup used in the mechanism of FIGS. 1-5.
Figure 12:
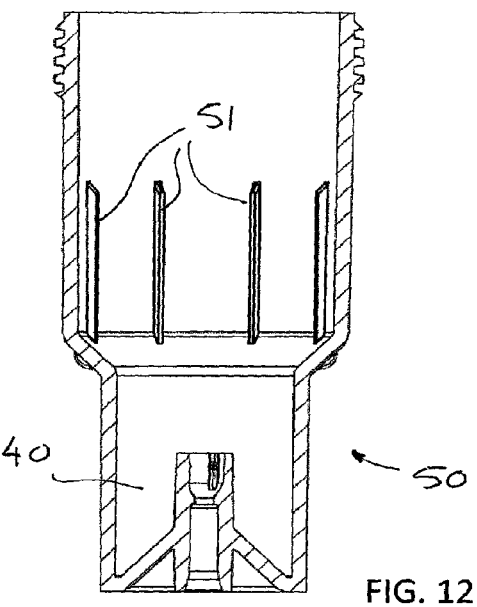
FIG. 12 is a sectional view taken along line 12-12 in FIG. 11.
Figure 13:
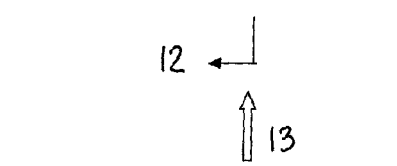
FIG. 13 is an end view of the piston cylinder cup, looking in the direction of the arrow 13 in FIG. 11.
Figure 15:
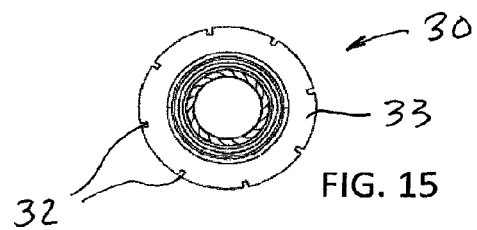
FIG. 15 is an end view of the piston housing, looking in the direction of the arrow 15 in FIG. 14.
Figure 14:
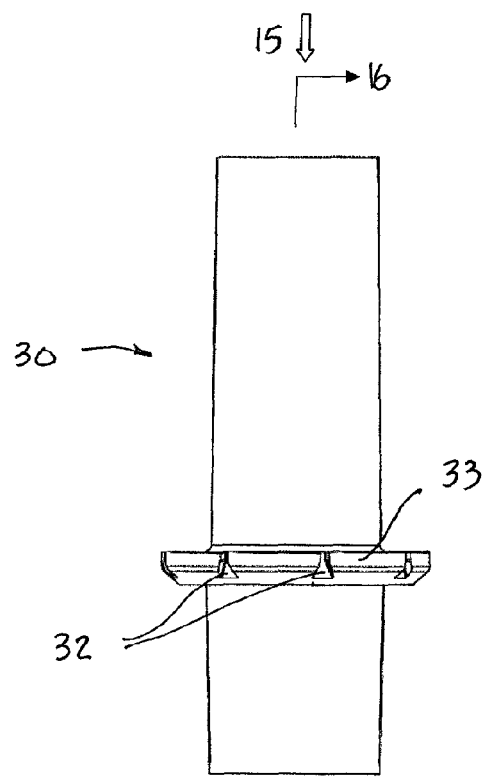
FIG. 14 is a side view in elevation of the piston housing used in the mechanism described herein.
Figure 16:
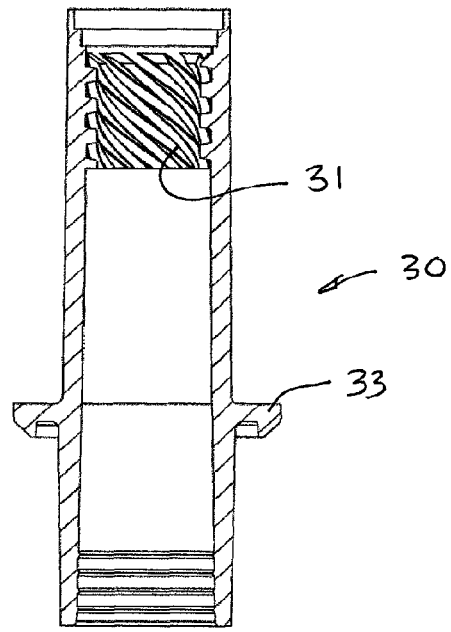
FIG. 16 is a sectional view taken along line 16-16 in FIG. 14.
Figure 18:
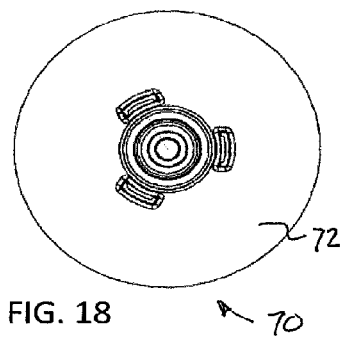
FIG. 18 is an end view of the drive screw, looking in the direction of the arrow 18 in FIG. 17.
Figure 19:
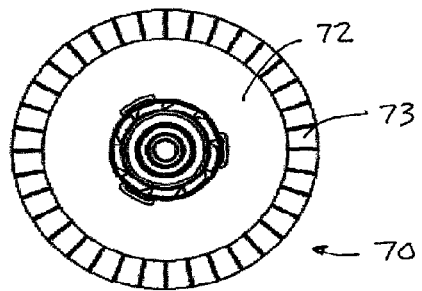
FIG. 19 is an end view of the drive screw, looking in the direction of the arrow 19 in FIG. 17.
Figures 17, 20, 21:
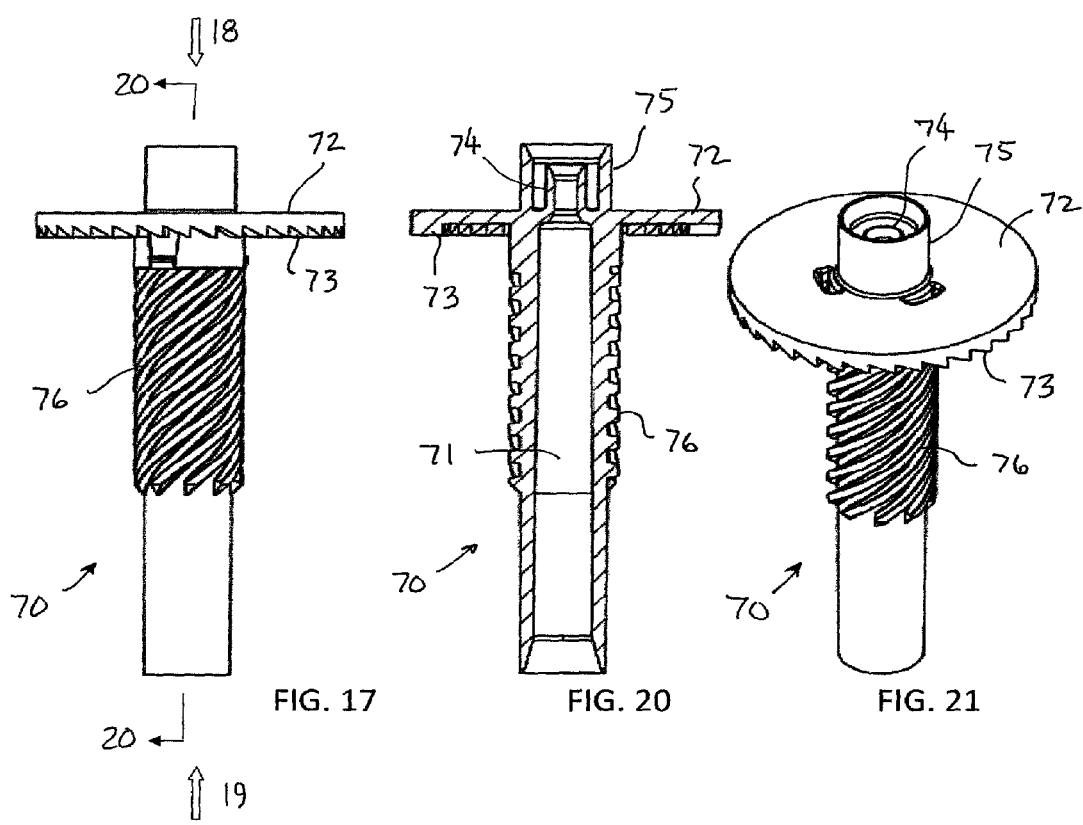
FIG. 17 is a side view in elevation of the drive screw used in the mechanism of the invention.
FIG. 20 is a longitudinal sectional view taken along line 20-20 in FIG. 17.
FIG. 21 is a top isometric view of the drive screw.
Figure 22:
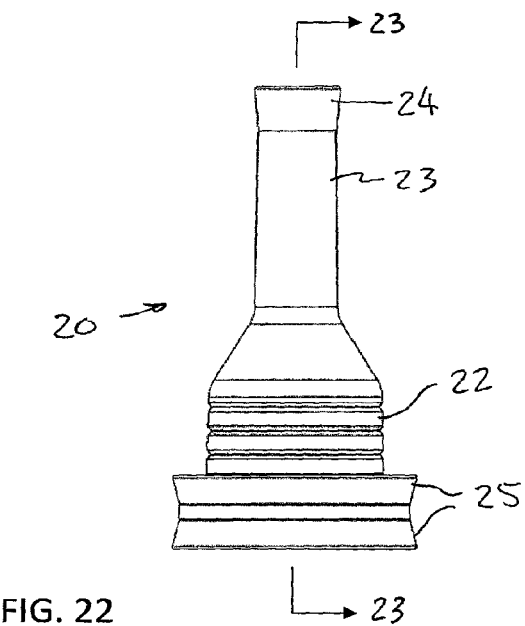
FIG. 22 is an enlarged side view in elevation of the piston used in the mechanism of the invention.
Figure 23:
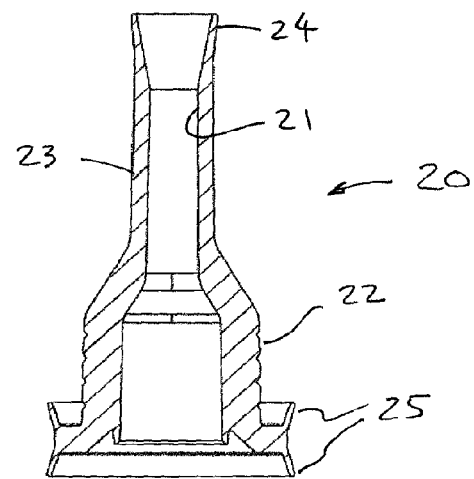
FIG. 23 is a sectional view taken along line 23-23 in FIG. 22.
Figure 24:
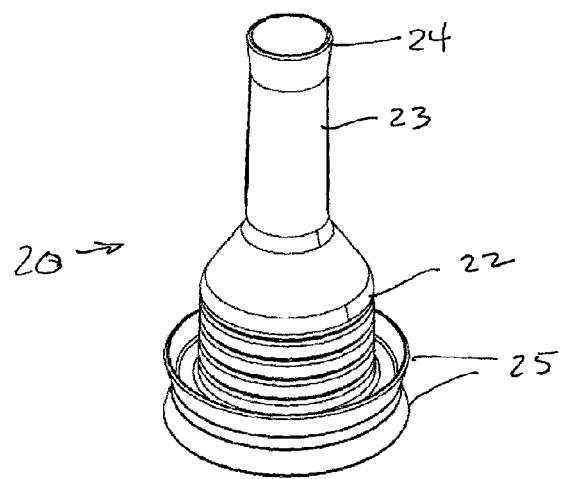
FIG. 24 is a top isometric view of the piston.
Figure 26:
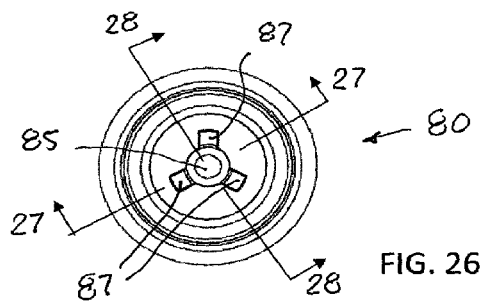
FIG. 26 is an end view of the stem valve, looking in the direction of arrow 26 in FIG. 25.
Figure 25:
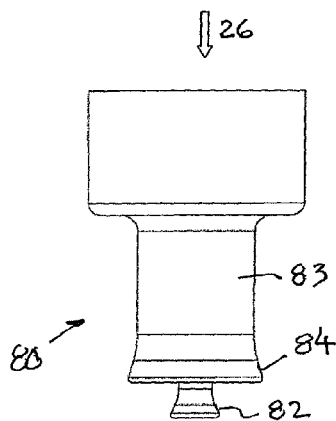
FIG. 25 is a side view in elevation of the stem valve used in the mechanism of the invention.
Figure 27:
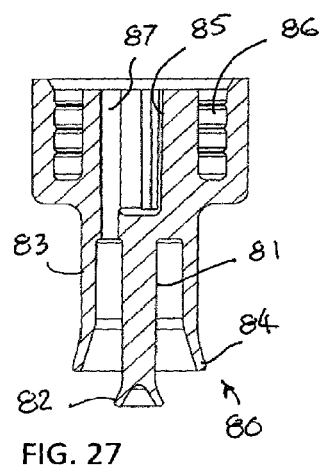
FIG. 27 is a sectional view taken along line 27-27 in FIG. 26.
Figure 28:
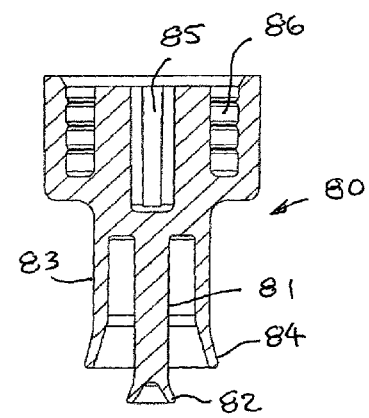
FIG. 28 is a sectional view taken along line 28-28 in FIG. 26.
Figure 29:
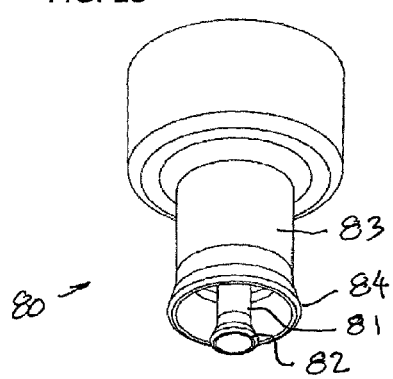
FIG. 29 is a bottom isometric view of the stem valve.
Figure 30:
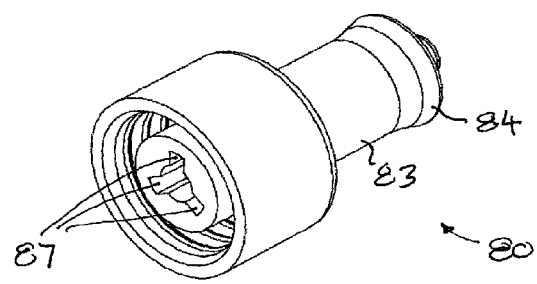
FIG. 30 is a top isometric view of the stem valve.
Figure 41:
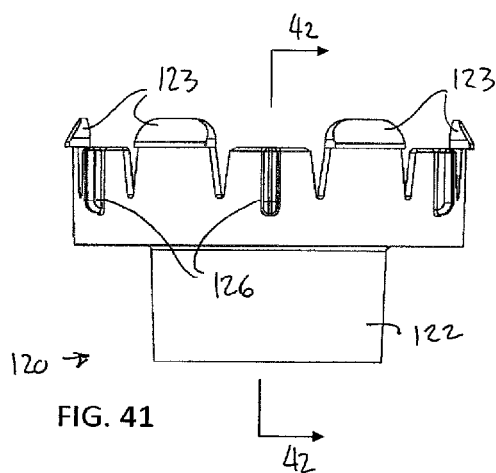
FIG. 41 is a side view in elevation of the clutch disc used in the escapement mechanism of the invention.
Figure 42:
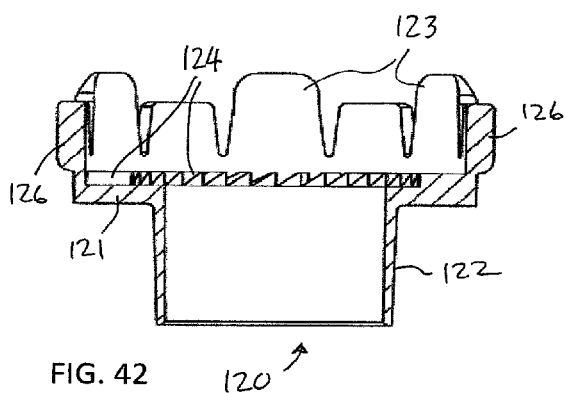
FIG. 42 is a longitudinal sectional view taken along line 42-42 in FIG. 41.
Figure 43:
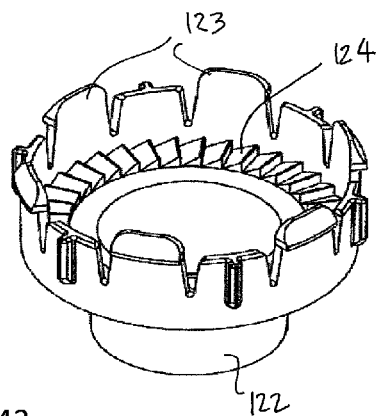
FIG. 43 is a top isometric view of the clutch disc.
Figure 44:
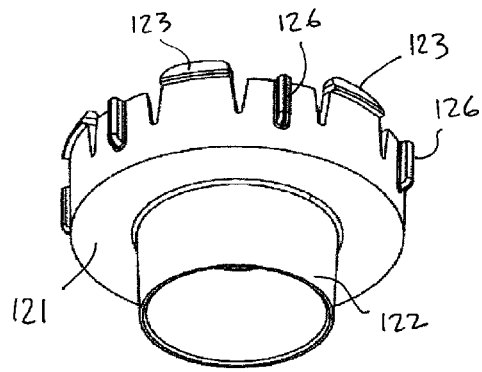
FIG. 44 is a bottom isometric view of the clutch disc.
Figure 45:
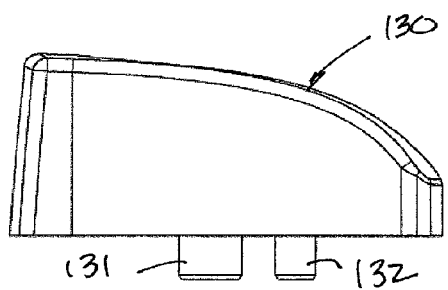
FIG. 45 is a side view in elevation of the actuator used in the mechanism of the invention.
Figure 46:
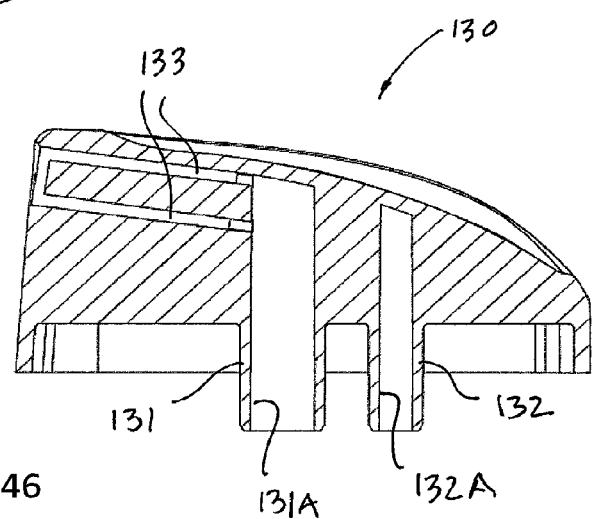
FIG. 46 is a longitudinal sectional view of the actuator.
Figure 47:
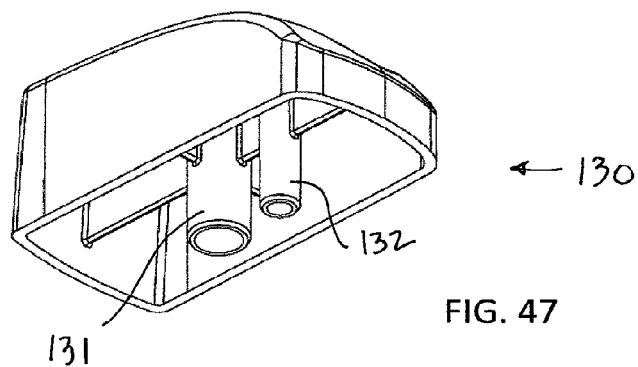
FIG. 47 is a bottom isometric view of the actuator.
Figures 56, 57:
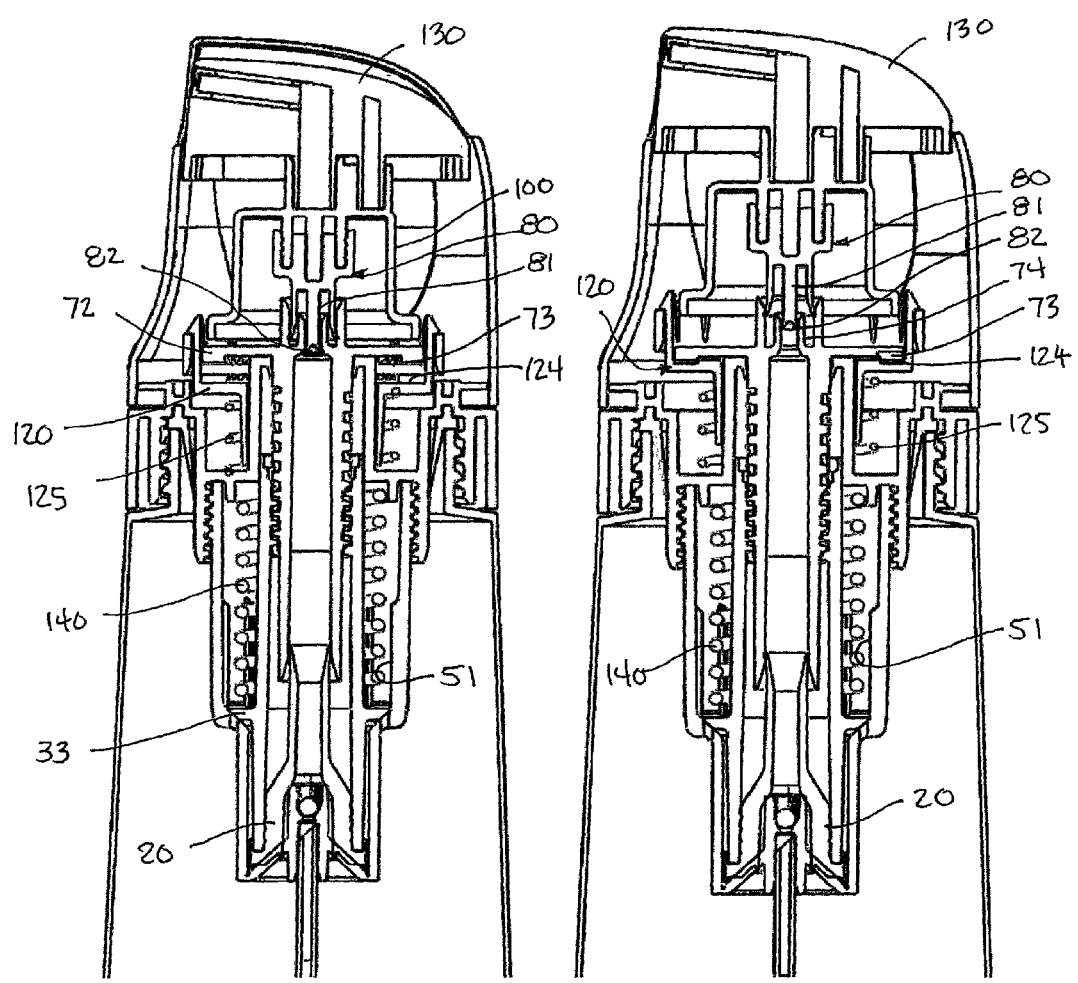
FIG. 56 is an enlarged fragmentary sectional view of the mechanism with the product emptied from the pressure chamber, the piston returned to its at-rest position, and the stem valve again returned to a sealed position while the clutch remains disengaged.
FIG. 57 is an enlarged fragmentary sectional view of the mechanism with the actuator, piston and stem valve all returned to their at-rest positions and the drive gear again engaged ready for another dispensing cycle.
Figure 60:
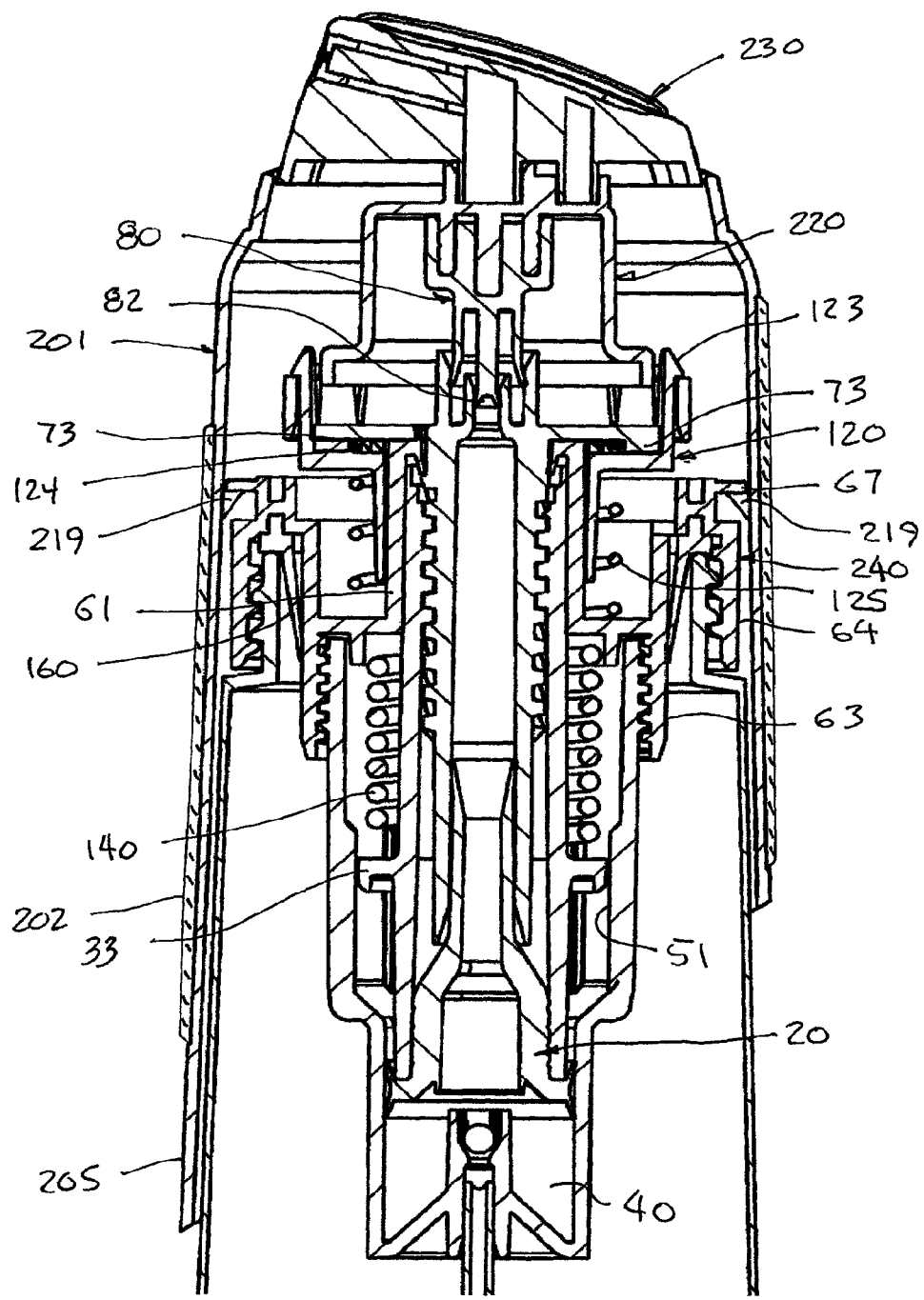
FIG. 60 is an enlarged fragmentary sectional view of the dispenser of FIGS. 58 and 59, showing the system in a fully charged position ready to dispense product.
Figure 61:
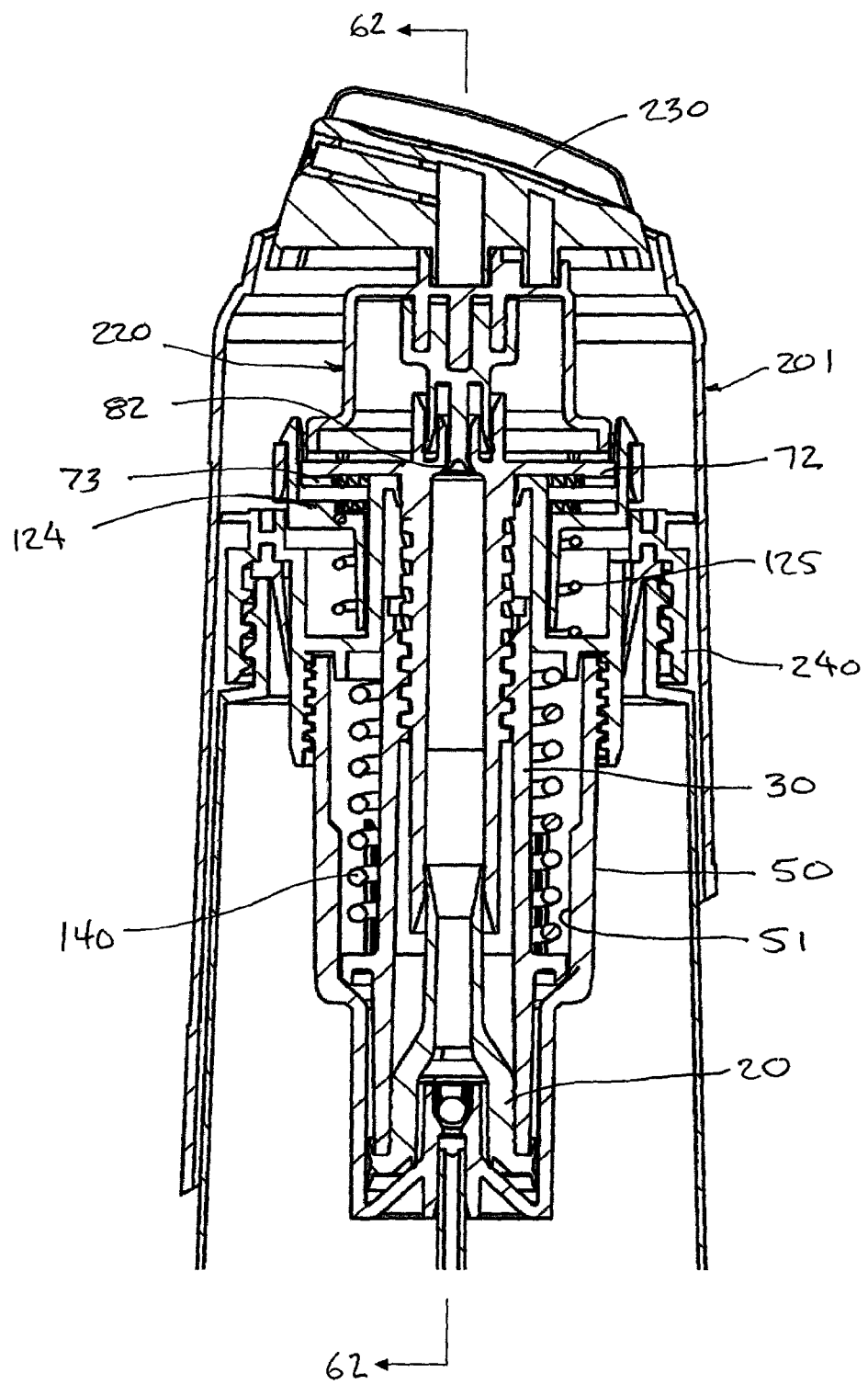
FIG. 61 is a view similar to FIG. 60, but with the actuator depressed and the stem valve open to permit discharge of product from the pump chamber, and showing the piston returned to its at-rest position.
Figure 62:
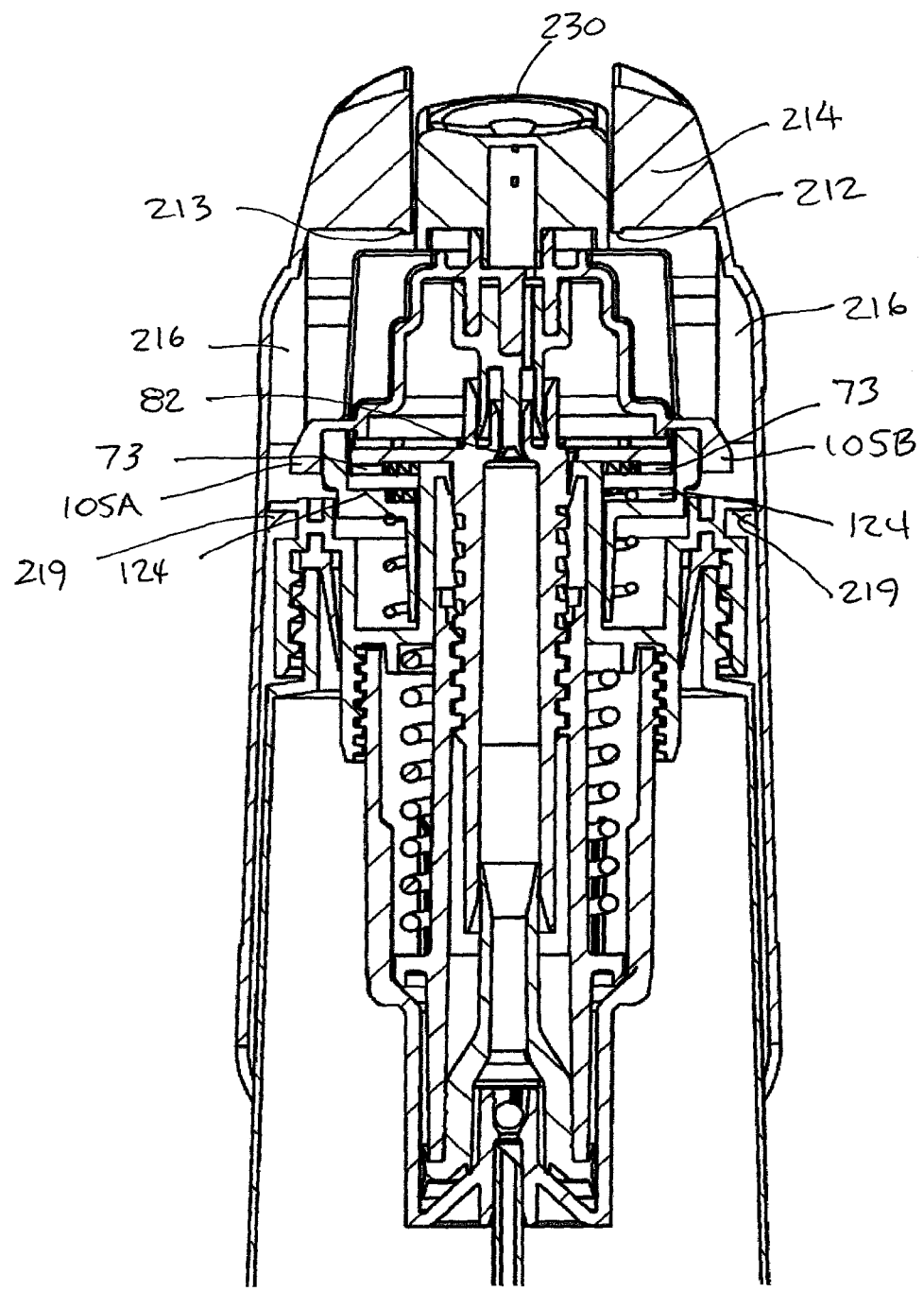
FIG. 62 is an enlarged fragmentary sectional view taken along line 62-62 in FIG. 61, showing the parts engaged between the actuator sleeve and actuator socket.
Figure 63:
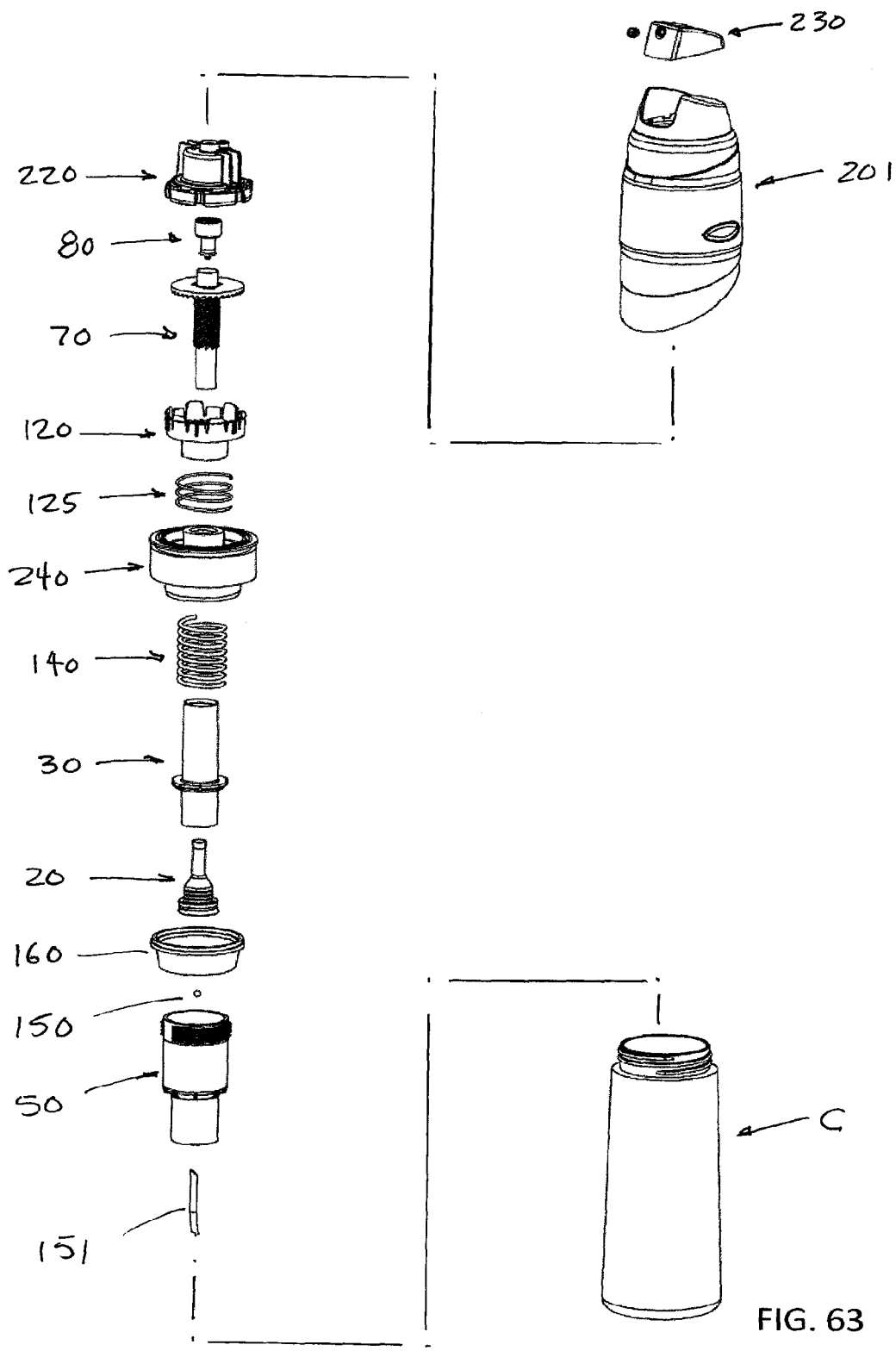
FIG. 63 is an exploded isometric view of the dispenser assembly of FIGS. 58-62.
Figure 64:
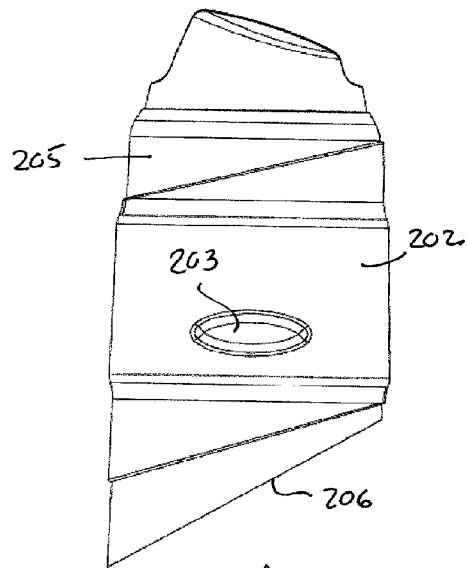
FIG. 64 is a side view in elevation of the modified actuator sleeve used in the assembly of FIGS. 58-62.
Figure 65:
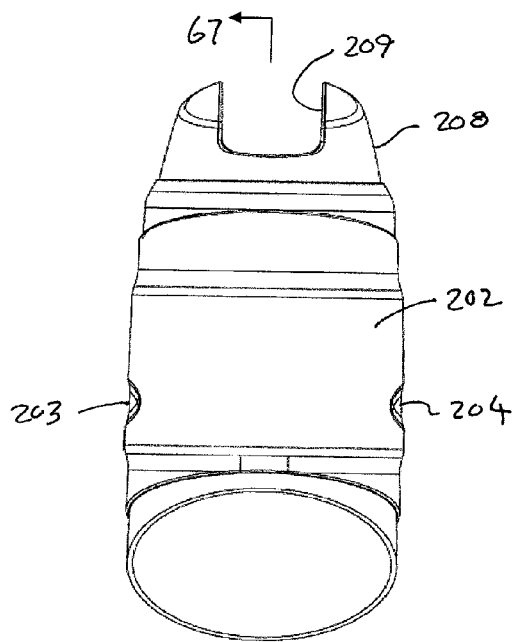
FIG. 65 is a rear view in elevation of the actuator sleeve.
Figure 66:
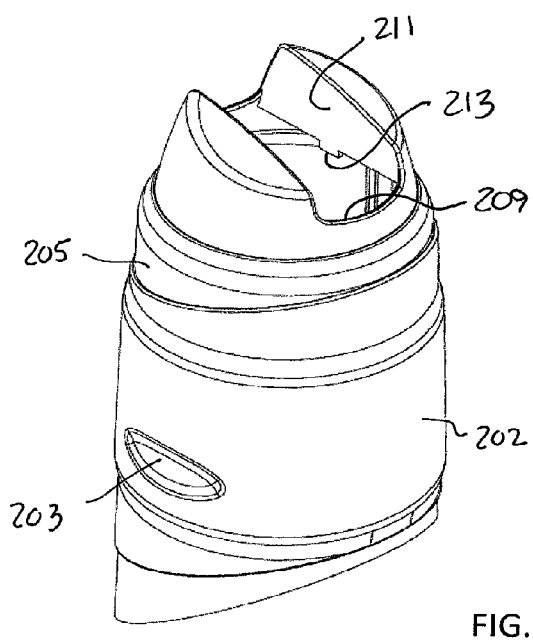
FIG. 66 is a top rear isometric view of the actuator sleeve.
Figure 67:
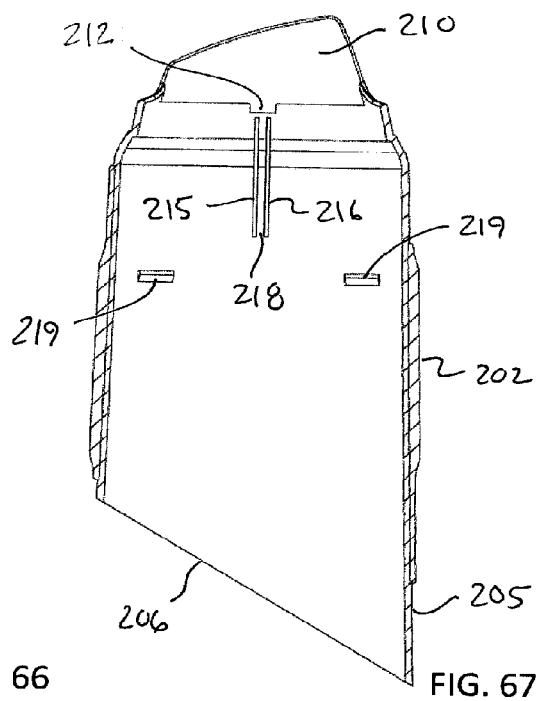
FIG. 67 is a view in section taken along line 67-67 in FIG. 65.
Figure 68:
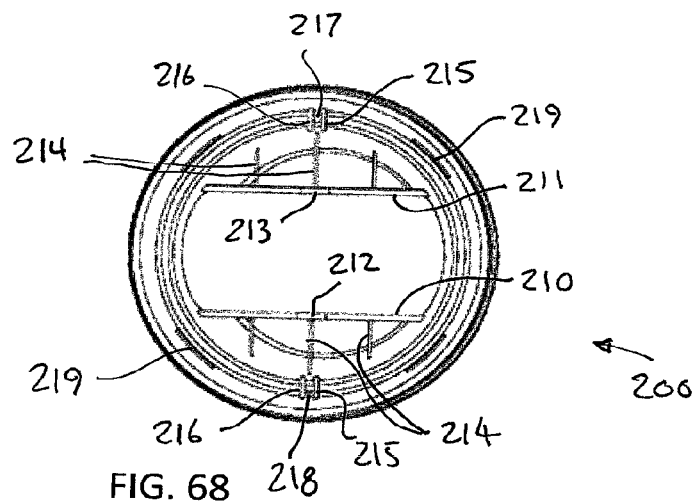
FIG. 68 is a bottom end view of the actuator sleeve, looking in the direction of the arrow 68 in FIG. 64.
Figure 69:
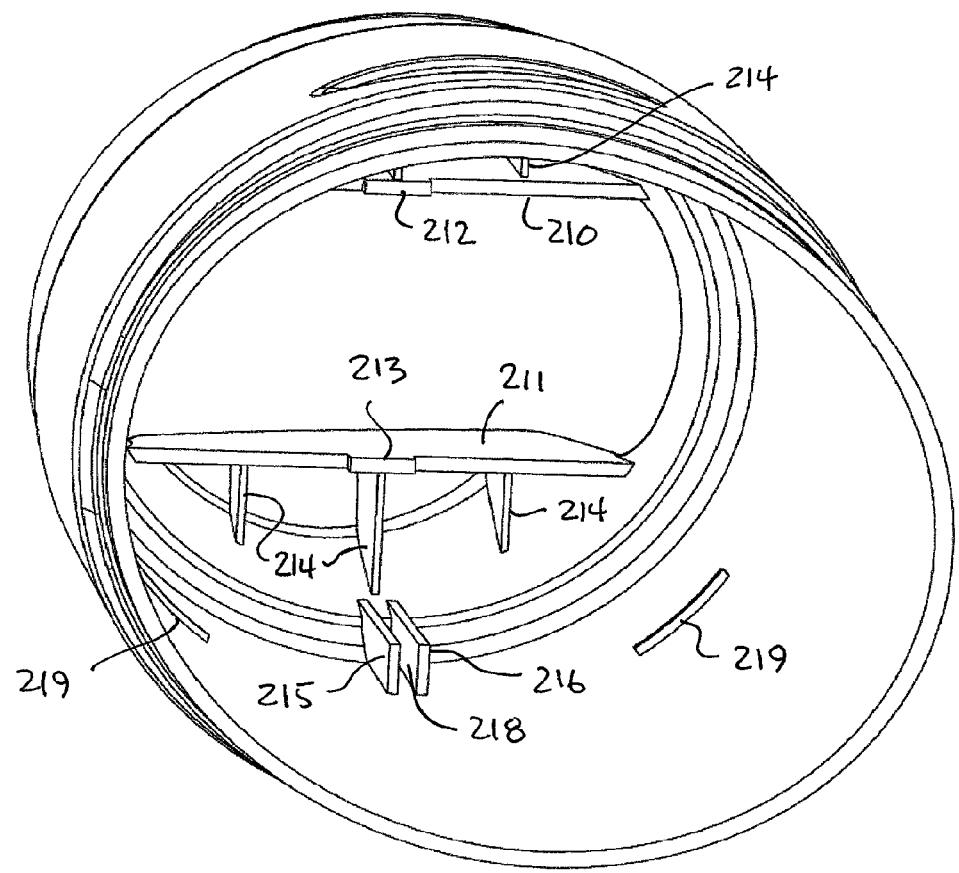
FIG. 69 is a greatly enlarged bottom isometric view of the actuator sleeve of FIGS. 64-68.
Figure 78:
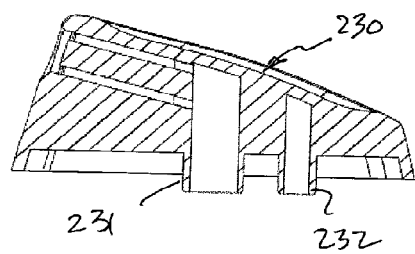
FIG. 78 is a view in section taken along line 78-78 in FIG. 77.
Figure 79:
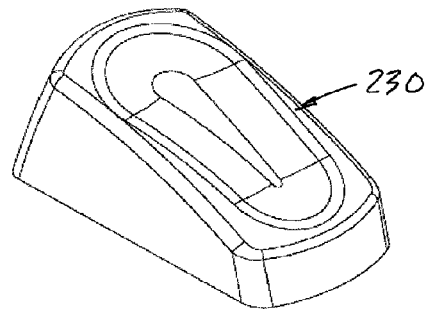
FIG. 79 is a top rear isometric view of the actuator.
Figure 76:
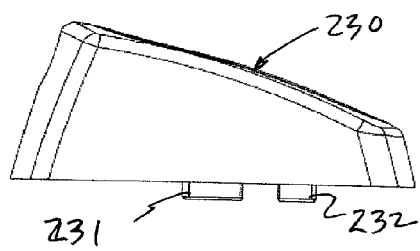
FIG. 76 is a side view in elevation of the actuator used in the assembly of FIGS. 58-62.
Figure 77:
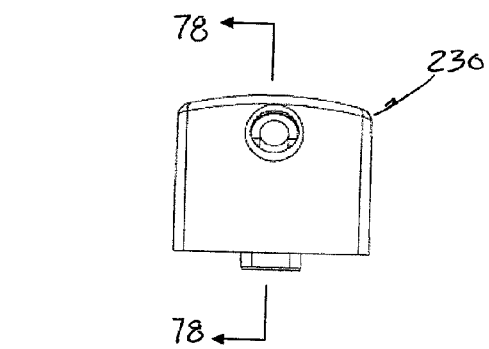
FIG. 77 is an end view in elevation of the actuator.
Figure 80:
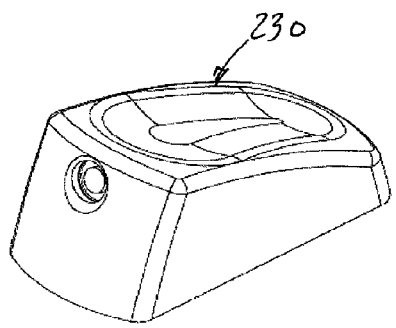
FIG. 80 is a top front isometric view of the actuator.
Figure 81:
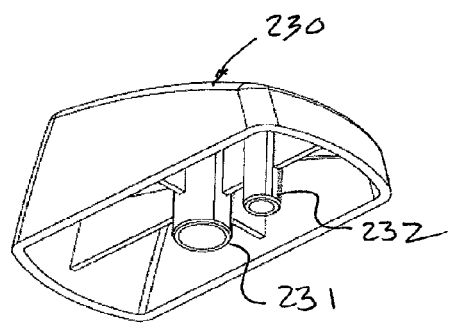
FIG. 81 is a bottom isometric view of the actuator.
Figure 82:
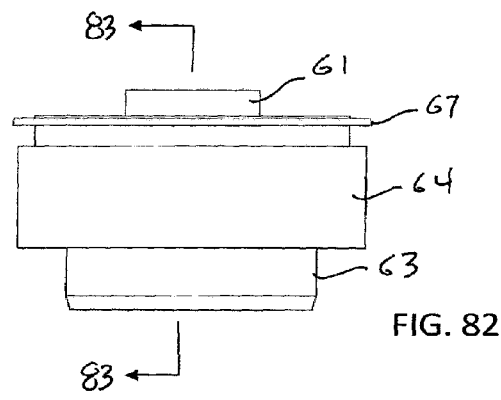
FIG. 82 is a side view in elevation of the cylinder cap used in the FIGS. 58-62 embodiment of the invention.
Figure 83:
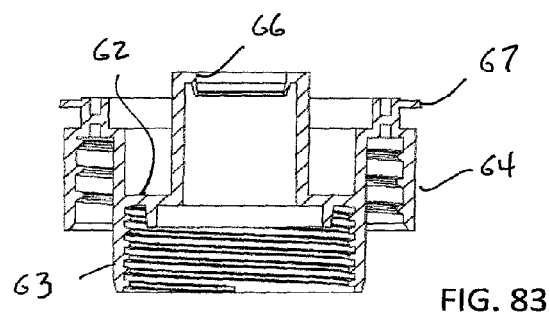
FIG. 83 is a longitudinal view in section taken along line 83-83 in FIG. 82.
Figure 84:
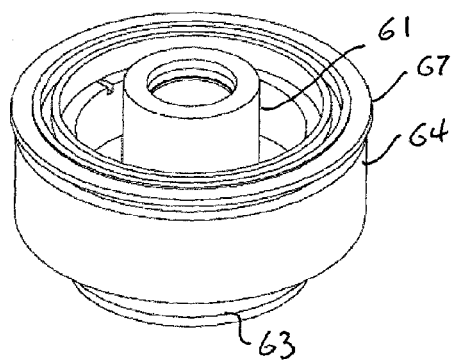
FIG. 84 is a top isometric view of the cylinder cap.
Figure 85:
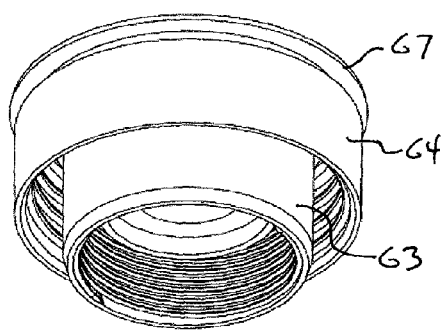
FIG. 85 is a bottom isometric view of the cylinder cap.
Figure 86:
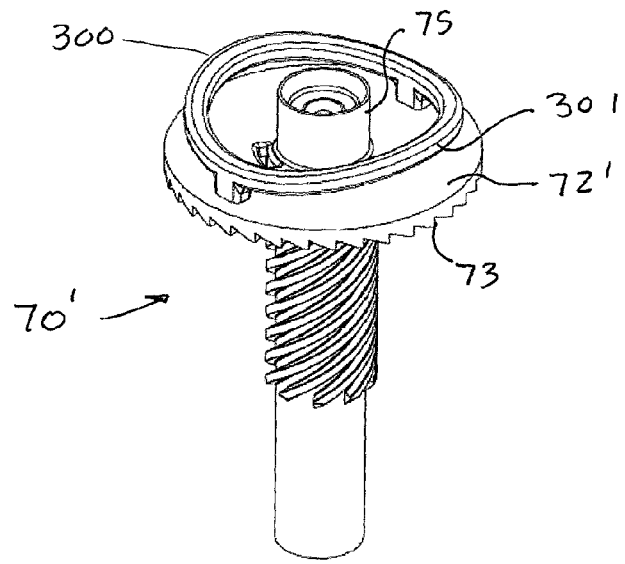
FIG. 86 is a top isometric view of an alternate form of drive screw that can be used in any of the forms of the invention disclosed herein.
Figure 87:
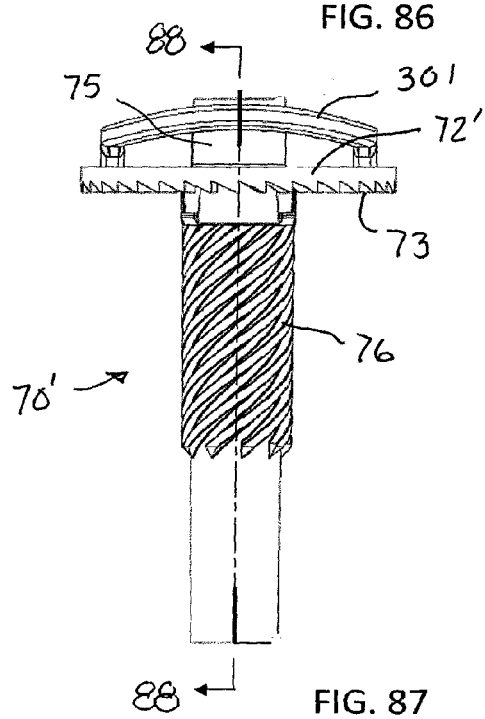
FIG. 87 is a side view in elevation of the drive screw of FIG. 86.
Figure 88:
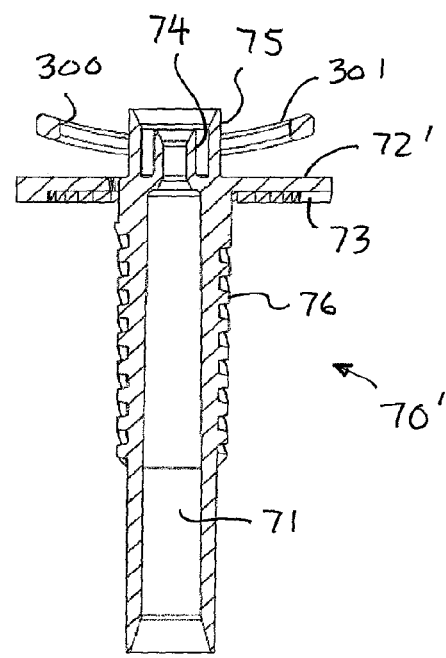
FIG. 88 is a longitudinal sectional view taken along line 88-88 in FIG. 87.

A first preferred embodiment of the invention is indicated generally at 10 in FIGS. 1-57. In this embodiment, a power assembly 11 comprising a pump mechanism 12 and actuator mechanism 13 are attached to the upper end of a container C for pressurizing and dispensing product from the container.

The pump mechanism 12 comprises a tubular piston 20 carried by a cylindrical piston housing 30 for reciprocation of the piston in a pump chamber 40 in the lower end of a cylinder cup 50 attached to a container cap 60 that is secured to the upper end of container C. The bottom end of the cylinder cup 50 contains a one-way ball check valve 150 connected with a dip tube 151 to permit flow of product from the dip tube and into the pump chamber but prevent reverse flow from the pump chamber back into the dip tube.

As seen best in FIGS. 3-5 and 7-13, the upper end of the piston housing 30 is slidably received in a first cylindrical wall 61 extending upwardly from the inner margin of a first annular wall 62 on the container cap 60, and the upper end of the cylinder cup 50 is threaded to a second cylindrical wall 63 depending from the outer margin of the annular wall 62. A third cylindrical wall 64 depending from the outer margin of a second annular wall 65 vertically offset and radially outwardly spaced from the first annular wall is threaded onto the upper end of the container to secure the container cap to the container. A radially inturned flange 66 on the upper end of the first cylindrical wall 61 extends inwardly over the upper end of the piston housing to help retain it assembled to the container cap, and an actuator sleeve retaining flange 67 extends outwardly from the top of the container cap above the depending cylindrical wall 64 for engaging detents on an actuator sleeve to retain it assembled to the container cap as described hereinafter. An outer skirt 68 depends from the outer edge of annular wall 65 in outwardly spaced relation to depending wall 64. The outer surface of the skirt is substantially flush with the outer surface of the container and provides a smooth outer finish to the dispenser. A vent gasket 160 is engaged between the second annular wall 65 of the container cap and the upper end of the container to vent the container as product is depleted from it.

The piston housing and piston are caused to reciprocate by a drive screw 70 extended coaxially into the piston housing. As seen best in FIGS. 18-21, the drive screw has a bore 71 extending axially therethrough and a radially outwardly extending annular flange 72 on its upper end, with a ring of gear teeth 73 on the underside of the flange. A valve seat tube 74 extends upwardly from the upper end of the drive screw at the upper end of the bore 71, and a cylindrical wall 75 extends upwardly in coaxial relation to the valve seat tube. Helical threads 76 on the outside of the upper end of the drive screw below the flange 72 are engaged with helical threads 31 in the piston housing, and splines 51 on the interior surface of the cylinder cup 50 are engaged in notches 32 in the outer periphery of a flange 33 on the piston housing to constrain the piston housing against rotation, whereby when the drive screw is rotated the interengaged helical threads cause the piston housing and piston to reciprocate in a first direction to enlarge the pump chamber and draw product into it.

As seen best in FIGS. 3-5 and 22-24, the piston 20 has an axial bore 21 therethrough and a main body portion 22 secured in the lower end of the piston housing. An elongate upper end 23 of the piston extends into the bore 71 of the drive screw and has an outwardly flared seal 24 on its upper end slidably sealed in the bore 71 to prevent leakage of product past the piston 20 from the drive screw bore 71. A flared seal ring 25 on the lower end of the piston extends outwardly beneath the lower end of the piston housing and into sliding sealed relationship with the interior surface of the pump chamber 40.

As the piston housing 30 and piston 20 are reciprocated upwardly to draw product into the pump chamber 40, a power spring 140 engaged between the flange 33 on the piston housing and the annular wall 62 on the container cap is compressed to store energy and urge the piston housing and piston in a return direction to exert pressure on the product in the pump chamber.

A stem valve 80, seen best in FIGS. 3-5 and 25-30, has a valve member 81 depending therefrom with an outwardly flared seal 82 on its bottom end slidably received in and sealed to the valve seat tube 74 on the drive screw. A cylindrical extension 83 depends in coaxial relation to the valve member 81 and has an outwardly flared seal 84 on its lower end slidably sealed with the inner surface of the cylindrical wall 75 extending upwardly around the seat tube. As long as the seal 82 is engaged in the seat tube 74 flow of product from the pump chamber 40 is blocked. A center bore 85 and an annular channel 86 are formed in the upper end of the stem valve to secure the stem valve to an actuator socket 100 as described hereinafter. Flow passages 87 are formed through the stem valve between the center bore and annular channel to permit flow of product through the stem valve from the bore of the drive screw when the stem valve is in open position. As long as the flared seal 82 is anywhere within the length of the seat tube 74 the stem valve is in closed position and flow therethrough is prevented, but as soon as the flared seal 82 extends below the inner surface of the seat tube the valve is open and flow is permitted upwardly through the stem valve.

The actuator mechanism 13 comprises a rotatable actuator sleeve 90 connected with an actuator socket 100 to rotate it, a clutch disc 120 releasably connected to the drive screw and having a plurality of latches 123 locking it to the actuator socket to rotate the drive screw when the actuator sleeve is rotated, and an actuator 130 attached to the actuator socket to reciprocate it and the clutch disc to disengage the clutch disc from the drive screw when the actuator is at least partially depressed and to reciprocate the stem valve 80 attached to the actuator socket to open the stem valve when the actuator is fully depressed.

The actuator sleeve 90, seen best in FIGS. 3-5 and 31-35, has a cylindrical side wall 91 with a circular base 92 and an upper portion 93 having an oblong opening 94 in its top through which the actuator 130 is received. Diametrically opposed tabs 95A and 95B depend into the housing from the upper end of the side wall at opposite sides of the opening 94, and pairs of closely spaced parallel tabs 96 and 97 on the inner surface of the housing at its opposite sides near its base define diametrically opposed slots 98A and 98B that are in general vertical alignment with the tabs 95A and 95B. A plurality of circumferentially spaced detents 99 on the inside of the circular base are engaged beneath the outer edge of the annular flange 67 on the upper end of the container cap 60 to retain the actuator sleeve on the container cap.

The actuator socket 100, seen best in FIGS. 3-5 and 36-40, has an upstanding cylindrical side wall 101 with a radially outwardly extending stepped annular flange 102 on its bottom end. A short cylindrical wall 103 depends from the outer edge of flange 102, and a plurality of slots 104 formed through the base of the flange in spaced relationship around its circumference receive the latches 123 on the clutch disc 120 (FIGS. 41-44) to lock the clutch disc to the actuator socket. Radially outwardly formed enlargements 110 on the wall 103 form circumferentially spaced slots 111 around the interior of the wall 103 for receiving ribs 126 on the clutch disc, described below. Tabs 105A and 105B projecting outwardly from diametrically opposite sides of wall 103 at the base of the actuator socket are engaged in the slots 98A and 98B on the interior of the actuator sleeve base to impart rotation to the actuator socket when the actuator sleeve is rotated. Pairs of spaced apart vertically extending parallel flanges 106A and 106B extending upwardly along respective diametrically opposite sides of the outer surface of the side wall 101 define channels 107A and 107B in which the tabs 95A and 95B on the inner upper surface of the actuator sleeve are received to also impart rotation to the actuator socket when the actuator sleeve is rotated. The upper end of wall 101 is closed by an end wall 108 having a first cylindrical socket 109A extending upwardly from its center, and a second smaller cylindrical socket 109B extending upwardly beside the first post. A post 112 depends from the center of wall 108 in coaxial alignment with the socket 109A, and a cylindrical wall 113 depends from wall 108 in outwardly spaced concentric relationship to the post 112. A plurality of openings 114 are formed through the wall 108 in the space between the post 112 and wall 113 to enable product to flow through the actuator socket during a dispensing cycle.

Depending posts 131, 132 on the actuator 130 are frictionally engaged in the sockets 109A and 109B, respectively, to hold the actuator to the actuator socket. The pin 112 extending downwardly from the center of the end wall 108 is frictionally engaged in the center bore 85 in the upper end of the stem valve 80, and the cylindrical wall 113 is frictionally engaged in the annular channel 86 surrounding the bore 85 to hold the stem valve to the actuator socket.

Clutch disc 120, seen best in FIGS. 3-5 and 41-44, comprises an annular wall 121 with a cylindrical wall 122 depending from its inner margin and the plurality of latches 123 projecting upwardly from its outer margin in spaced apart relationship around its circumference. A plurality of longitudinally oriented ribs 126 on the outer surface of wall 122 engage with the slots 111 in the actuator socket 100 to aid in imparting rotation to the clutch disc when the actuator socket is rotated. The depending cylindrical wall 122 is rotatable and axially slidable on the first cylindrical wall 61 projecting upwardly from the container cap 60, and the annular wall 121 underlies the annular flange 72 on the drive screw and has a ring of gear teeth 124 on its upper surface urged into engagement with the gear teeth 73 on the underside of the drive screw flange 72 by an actuator return spring 125 engaged between the annular wall 121 on the clutch disc and the first annular wall 62 on the container cap.

The posts 131 and 132 on the actuator 130 have respective bores 131A and 132A therein. The bore 131A communicates at its inner end with a fluid passage 133 extending to a mechanical breakup unit (MBU), not shown, but the bore 132A dead-ends at its inner end.

Figure 48:
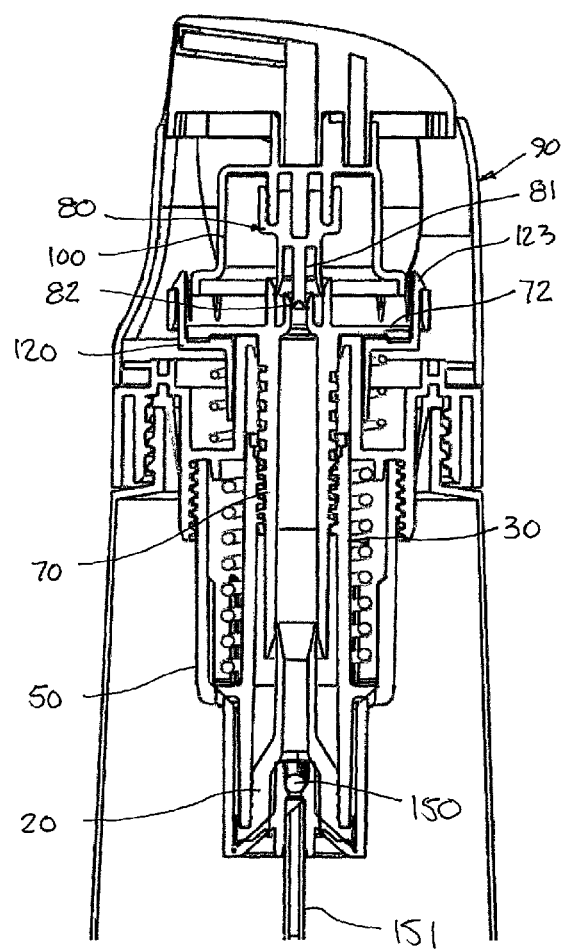
FIG. 48 is a fragmentary longitudinal sectional view of the mechanism at rest before the actuator sleeve is rotated to draw product into the pump chamber and store energy in the energy storage device, i.e., compress the power spring in the embodiment shown.
Figure 49:
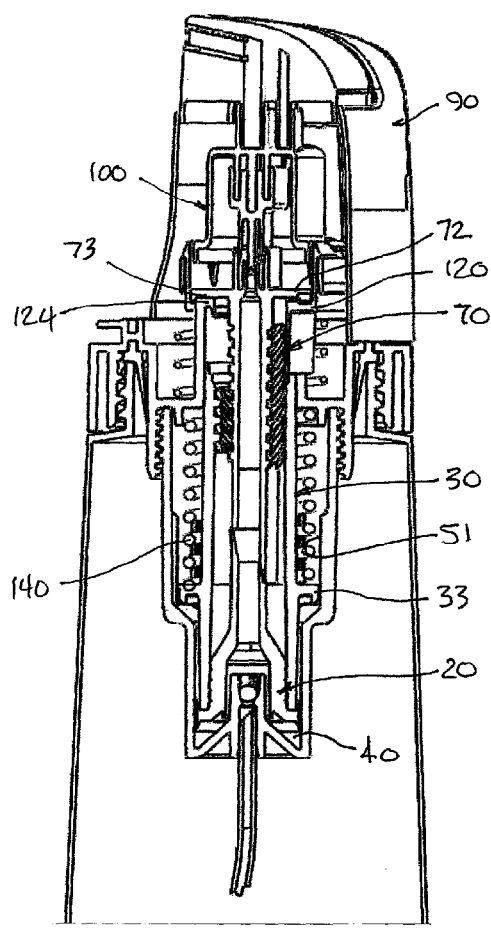
FIG. 49 is a fragmentary sectional view of the mechanism in the state it is in with the actuator sleeve partially turned approximately one-eighth revolution.
Figures 50, 51:
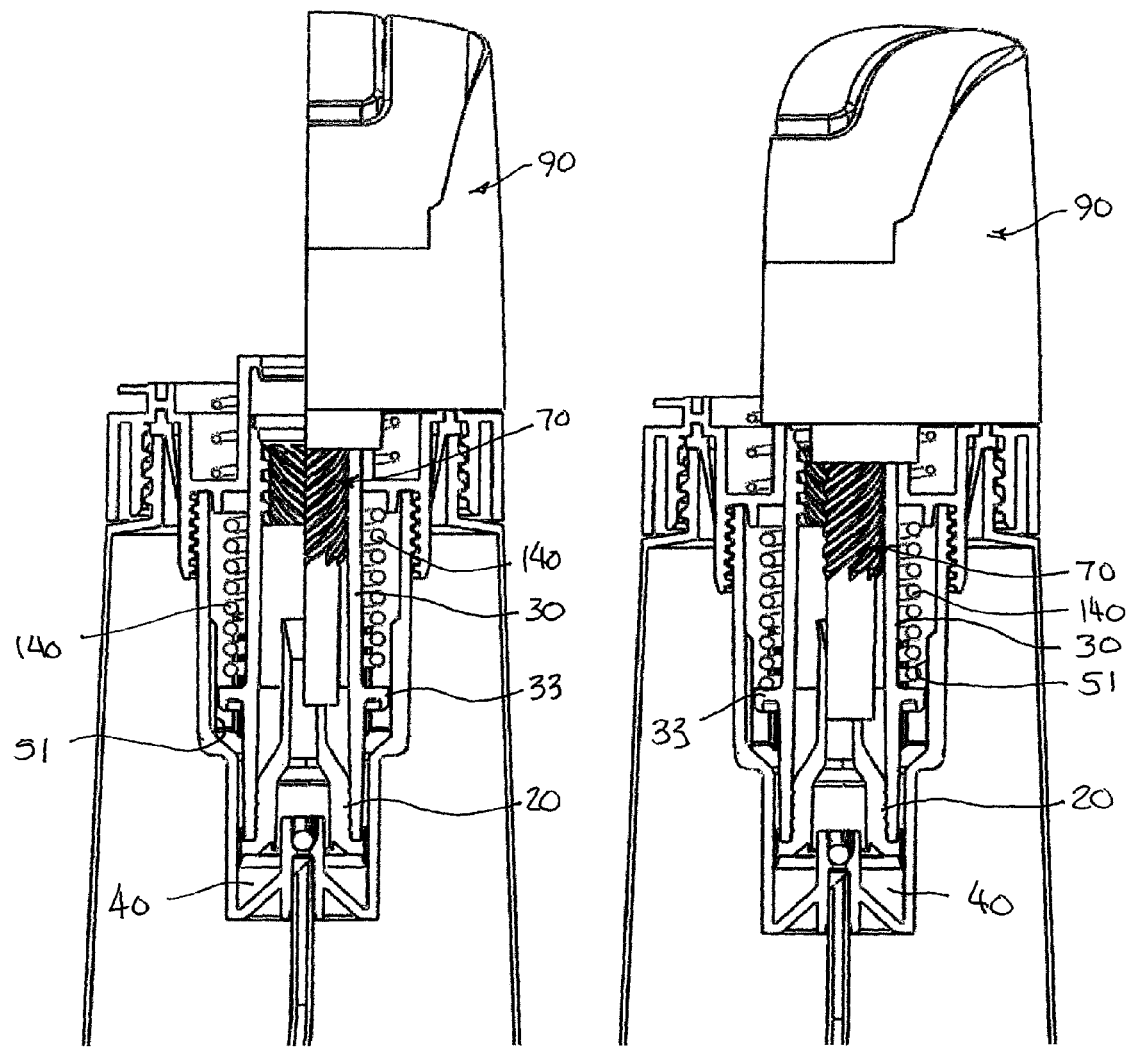
FIG. 50 is a fragmentary sectional view of the mechanism in the state it is in with the actuator sleeve turned approximately one-quarter revolution.
FIG. 51 is a fragmentary sectional view of the mechanism in the state it is in with the actuator sleeve turned approximately three-eighth revolution.

Actuation of the power assembly 11 to draw product into the pump chamber 40 and pressurize it for subsequent dispensing is illustrated in FIGS. 48-53. In FIG. 48 the mechanism is shown in its at-rest position with the piston 20 at the bottom of the pump chamber. As the actuator sleeve 90 is rotated through its operative range of motion as depicted in FIGS. 49-53, the actuator socket 100, clutch disc 120, and drive screw 70 are caused to rotate, pulling the piston housing 30 and piston 20 upwardly to draw product through the dip tube 151 and past the ball valve 150 into the pump chamber. This motion of the piston housing also compresses the power spring 140, which exerts pressure on the product in the pump chamber. The product is trapped in the pump chamber and the bores of the piston and drive screw by the ball valve 150 at the bottom of the pump chamber and the stem valve 80 at the top of the drive screw bore.

Figures 54, 55:
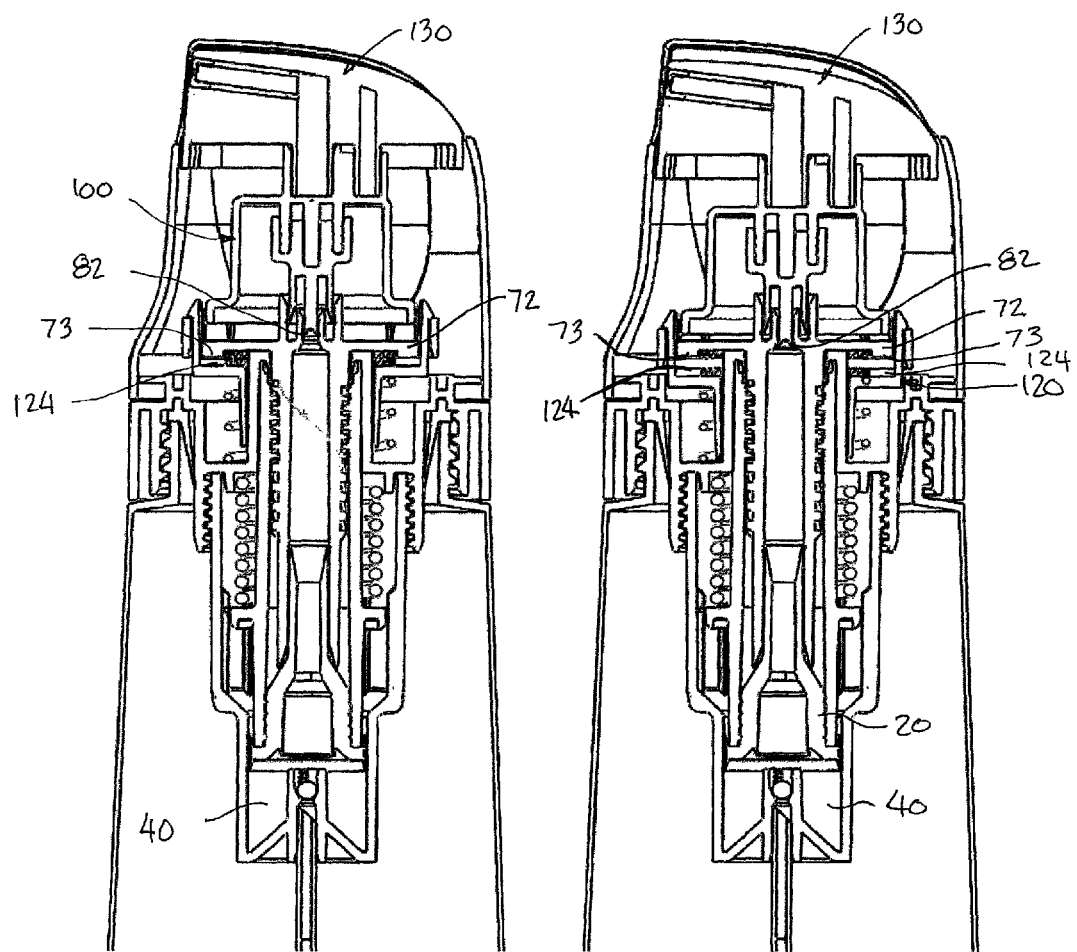
FIG. 54 is an enlarged fragmentary sectional view of the mechanism in FIG. 53, shown with the actuator partially depressed to disengage the clutch but with the stem valve still in a sealed position.
FIG. 55 is an enlarged fragmentary sectional view of the mechanism with the actuator fully depressed to move the stem valve to an unsealed position so that product can flow from the pump chamber and outwardly through the discharge nozzle.

Actuation of the power assembly to dispense the pressurized product from the pump chamber is illustrated in FIGS. 53-57. In FIG. 53 the piston and piston housing are in their positions with the pump chamber fully charged, and the actuator 130 is in its at-rest position. When the actuator is initially depressed, as shown in FIG. 54, the actuator socket 100, stem valve 80, and clutch disc 120 are moved downwardly, disengaging the gear teeth 124 on the clutch disc from the gear teeth 73 on the drive screw. Downward movement of the clutch disc also compresses the actuator return spring 125. During this time, because of the length of the seat tube 74, the seal 82 on the bottom end of the stem valve member 81 remains slidably engaged in the seat tube to trap product in the pump chamber and prevent movement of the piston and piston housing until the clutch disc has become disengaged from the actuator socket, thereby preventing rotation of the drive screw and actuator sleeve which would otherwise occur when the piston and piston housing move toward their at-rest positions. Further depression of the actuator 130, as depicted in FIGS. 55 and 56, moves the seal 82 out of the seat tube 74, permitting the product to be forced from the pump chamber by the spring 140. Since the clutch disc is disengaged from the drive screw at this time, return movement of the piston and piston housing toward their at-rest positions can cause rotation of the drive screw without causing rotation of the actuator socket and actuator sleeve.

Upon release of the actuator 130, the actuator return spring 125 urges the clutch disc 120, actuator socket 100, and actuator 130 back toward their at-rest positions as shown in FIG. 57. This results in the seal 82 on the stem valve 80 first entering the seat tube 74 to prevent further flow of product from the dispenser, and then re-engages the gear teeth 73 and 124 to ready the mechanism for a further dispensing cycle. Dispensing of product from the pump chamber can be accomplished in a single operation, or accomplished in steps until the pump chamber is emptied. FIG. 57 shows the power assembly returned to its at-rest position ready for another dispensing cycle as described above.

A modified dispenser assembly 200 is shown in FIGS. 58-85. This embodiment is constructed and functions substantially the same as the previous embodiment except that there are one or more differences in the construction of the actuator sleeve, actuator socket, actuator, and cylinder cap, and in the structure engaged between the actuator sleeve and actuator socket to cause rotation of the actuator socket when the actuator sleeve is rotated. All other components of the assembly, including the piston 20, cylindrical piston housing 30, pump chamber 40, cylinder cup 50, clutch disc 120, actuator return spring 125, power spring 140, one-way ball check valve 150 and dip tube 151 are constructed identically or substantially identically to those same parts in the previous embodiment and function in the same way.

In the dispenser assembly 200 the actuator sleeve 201 is elongate relative to the actuator sleeve 90 in the first embodiment, and extends at its bottom end a substantial distance down the outside of the container C. An outer sleeve 202 of relatively softer material is positioned on a central outer portion of the actuator sleeve and has slightly recessed gripping areas 203 and 204 on diametrically opposite sides thereof to facilitate gripping of the actuator sleeve to turn it. In a preferred construction, the sleeve is over-molded on the actuator sleeve. This sleeve may be omitted if desired.

As seen best in FIGS. 58-69, the actuator sleeve has a side wall 205 with a circular base closely rotationally received on the upper end of the side wall of the container. The side wall terminates in an angled lower end 206 with the longer part of the side wall oriented toward the front of the container C. The upper end 208 of the side wall has an ovoid shape in horizontal cross section and an oblong opening 209 in its top through which the actuator (described hereinafter) is received. Walls 210 and 211 extend downwardly from opposite sides of the opening 209, and short tabs 212 and 213 project downwardly from the center of the bottom edge of the walls 210 and 211. Reinforcing webs 214 extend between the walls 210, 211 and the adjacent upper end of the housing side wall 205. Pairs of closely spaced longitudinally extending parallel ribs 215 and 216 are on the inner upper surface of the housing at its opposite sides just below and in general vertical alignment with the tabs 212 and 213, defining elongate vertically extending slots 217 and 218, and a plurality of circumferentially spaced detents 219 are on the inside of the housing side wall 205 spaced a slight distance below the ribs 215 and 216 and circumferentially offset therefrom.

The actuator socket 220 in this embodiment, seen best in FIGS. 59-63 and 70-75, is the same as the actuator socket 100 in the previous embodiment except that the cylindrical sockets 221 and 222 extending upwardly from the end wall 108 have a reduced height relative to the sockets 109A and 109B in the first embodiment. All other parts in the actuator socket 220 are the same as in the previous embodiment and function the same way, and the parts are given the same reference numerals as the corresponding parts in the previous embodiment. Thus, the plurality of slots 104 formed through the base of the flange 102 receive the latches 123 on the clutch disc 120 to lock the clutch disc to the actuator socket. Tabs 105A and 105B projecting outwardly from diametrically opposite sides of wall 103 at the base of the actuator socket are engaged in the slots 217 and 218 on the interior of the actuator sleeve side wall, and tabs 212 and 213 extend into the channels 107A and 107B defined between the vertically extending parallel flanges 106A and 106B extending upwardly along respective diametrically opposite sides of the outer surface of the side wall 205 to impart rotation to the actuator socket when the actuator sleeve is rotated. A pin 112 extends downwardly from the center of the end wall 108, and a cylindrical retaining wall 113 extends downwardly in concentric relationship to the pin 112 for cooperation with the stem valve 80 just as in the previous embodiment. Thus, the pin 112 is frictionally engaged in the center bore 85 in the upper end of the stem valve 80, and the retaining wall 113 is frictionally engaged in the annular channel 86 surrounding the bore 85 to hold the stem valve to the actuator socket.

The actuator 230 in this embodiment is constructed substantially the same as the actuator 130 in the previous embodiment. It differs essentially in that the depending posts 231, 232 on the actuator 230 are slightly shorter than the posts 131 and 132 in the previous embodiment. Otherwise, the actuator 230 functions the same as the previous actuator 130. Thus, the posts 231 and 232 are frictionally engaged in the sockets 221 and 222, respectively, in the actuator socket 220 to hold the actuator to the actuator socket.

The entire assembly is held to the container C by a modified container cap 240 that differs from the previous container cap 60 only in that the outer depending cylindrical wall 68 is omitted. In all other respects the container cap 240 is constructed the same and functions the same as the previous container cap and corresponding parts are given the same reference numerals.

A modified power assembly according to the invention is shown in FIGS. 86-97. This form of the invention is constructed and functions the same as the first form of the invention shown in FIGS. 1-57 and described above, except that leaf spring members 300, 301 are integrally formed on top of the annular flange 72' on the drive screw 70'. These leaf spring members act between the clutch disc 120 and actuator socket 100 and function as an actuator return spring to move the actuator socket, clutch disc and actuator 130 to their upper at-rest positions. The leaf spring members 300, 301 may be used in combination with the return spring 125 as shown in these figures and used in the first two embodiments disclosed herein, or it may be used alone and the return spring 125 omitted (not shown).

Figure 89:
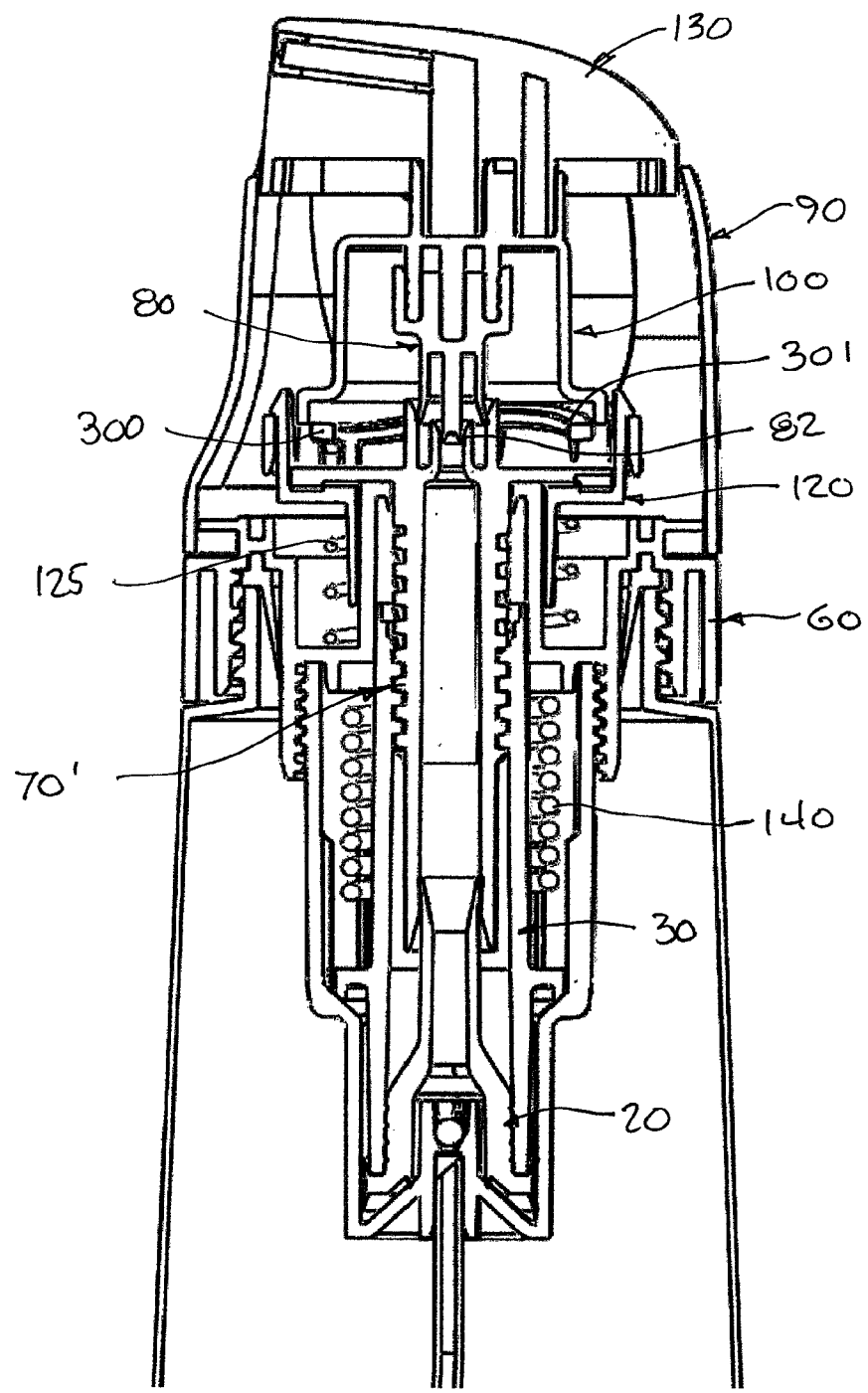
FIG. 89 is an enlarged fragmentary view in longitudinal section of that form of mechanism incorporating the modified drive screw of FIG. 86, shown in an at-rest position before being actuated to draw product into the pump chamber.
Figure 90:
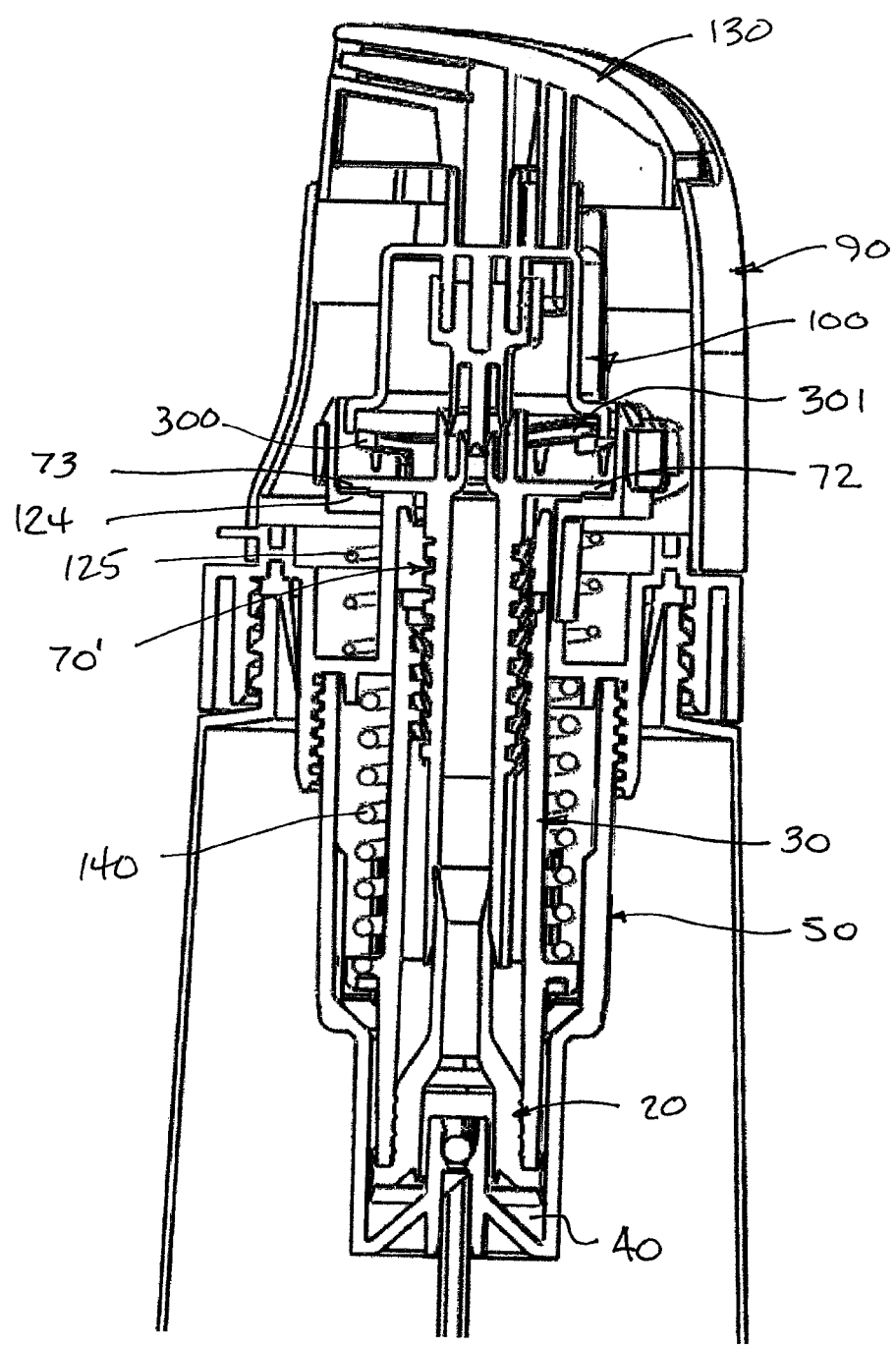
FIG. 90 is a view similar to FIG. 89 but showing the actuator sleeve partially rotated and the piston housing and piston partially moved from their at-rest position to draw product into the pump chamber.

Thus, FIG. 89 shows the mechanism with the actuator 130 and piston 20 in their at-rest positions, the gear teeth 73 on the underside of flange 72' of drive screw 70' engaged with the gear teeth 124 on top of the annular wall 121 of the clutch disc 120, and the stem valve 80 in its closed position.

Figure 91:
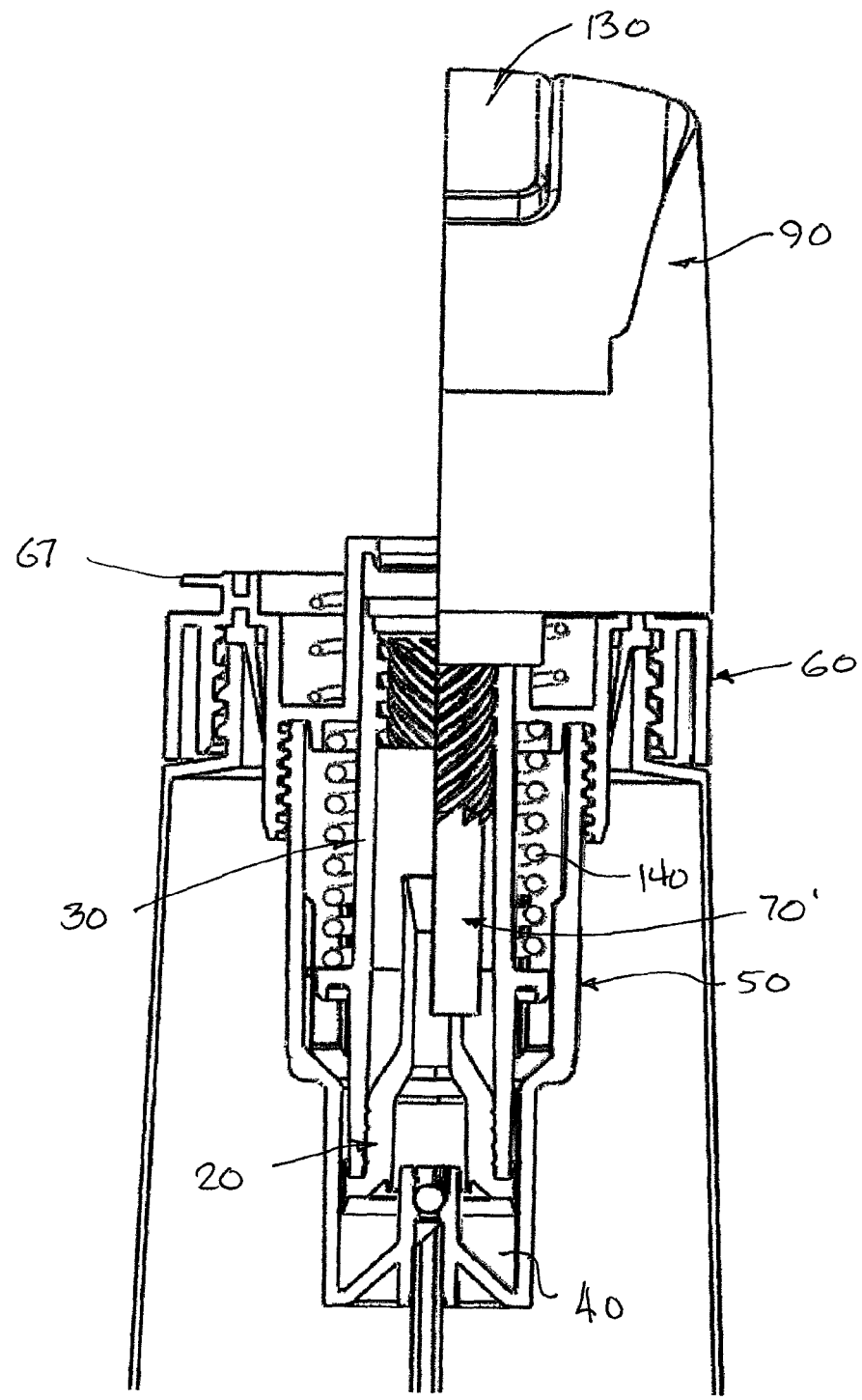
FIG. 91 is a view similar to FIG. 90 but showing the actuator sleeve rotated through approximately a quarter turn and the piston housing and piston moved farther in a direction to draw product into the pump chamber.
Figure 92:
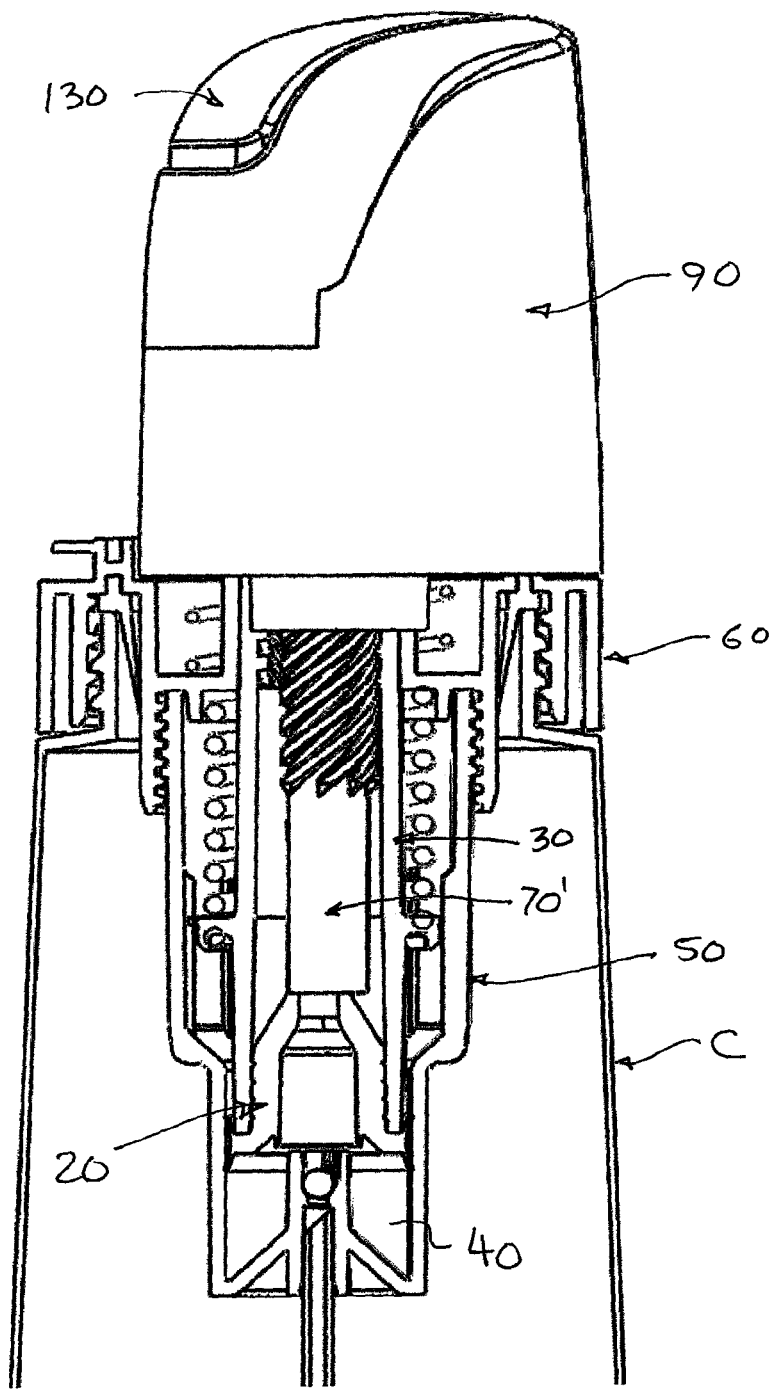
FIG. 92 is a view similar to FIG. 91 but showing the actuator sleeve rotated through about three-eighths of a revolution.
Figure 93:
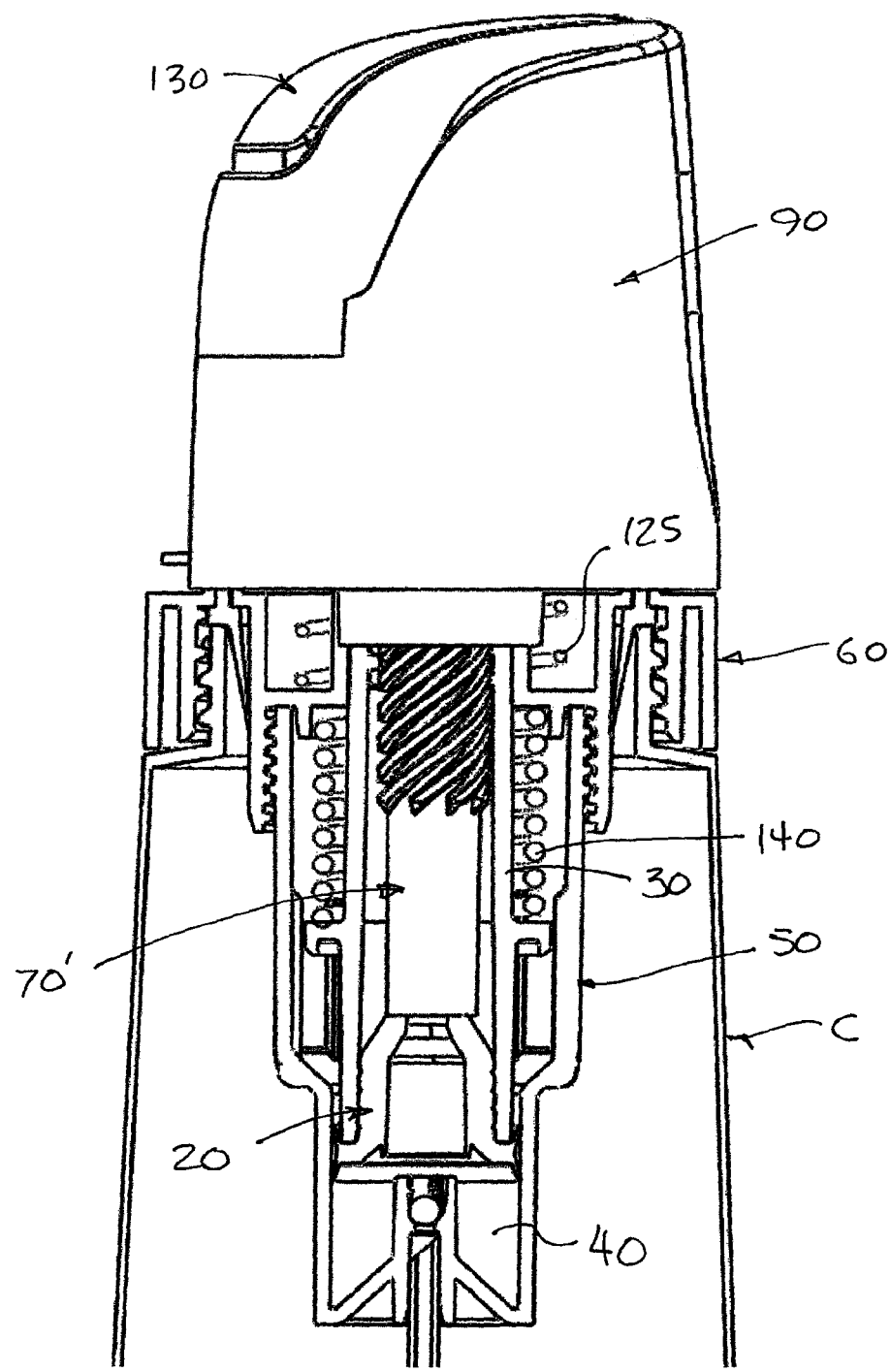
FIG. 93 is a view similar to FIG. 92 but showing the actuator sleeve rotated nearly one-half revolution and the pump chamber nearly fully charged.

FIGS. 91-93 show the actuator sleeve at various stages of rotation to turn the clutch disc and drive screw to raise the piston 20 to enlarge the pump chamber 40 and draw product into it in the same manner as previously described. This movement of the piston also compresses the power spring 140, storing energy that acts against the flange 33 on piston housing 30 to move the piston in a direction to exert pressure on the product in the pump chamber 40.

Figure 94:
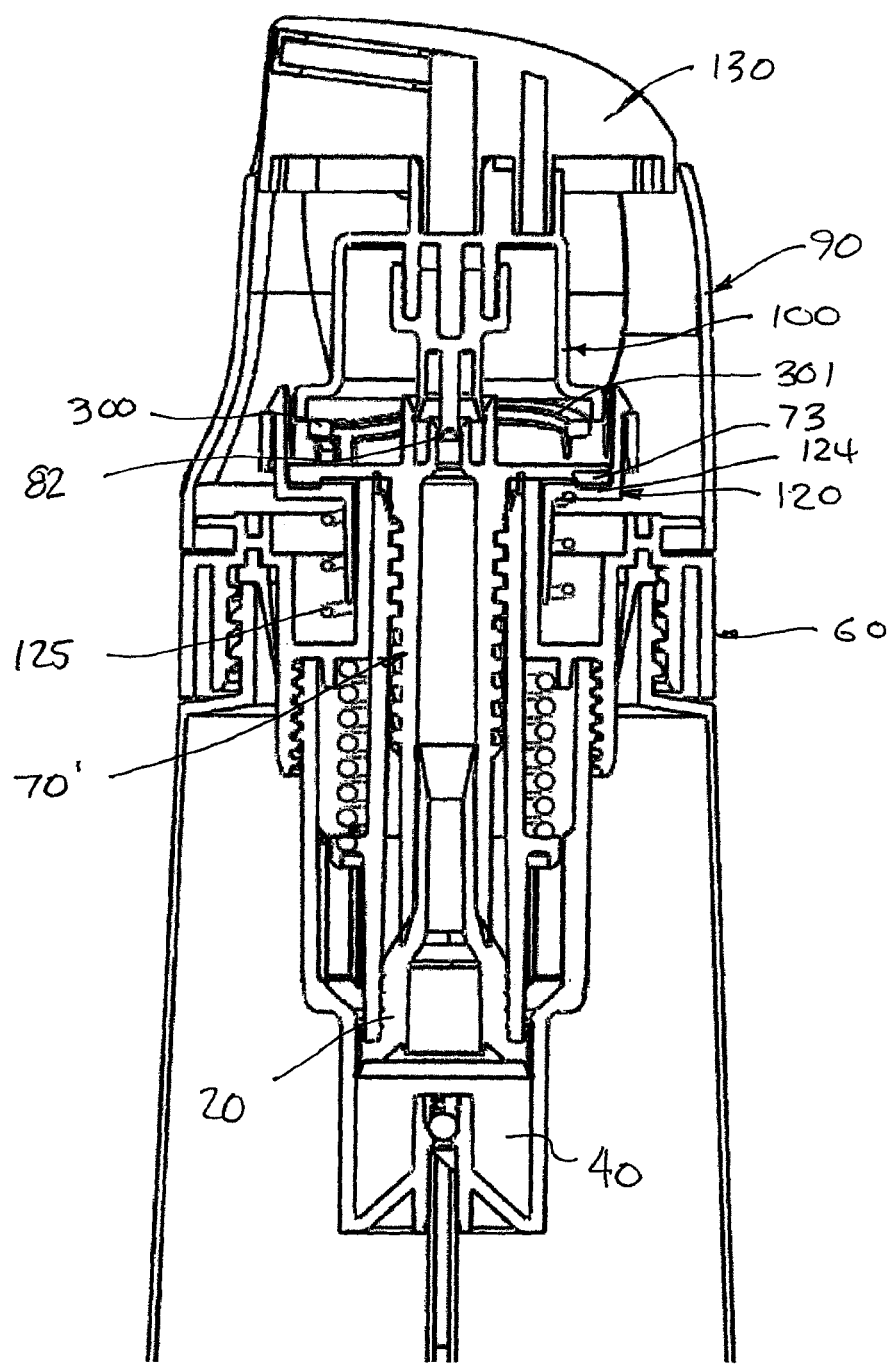
FIG. 94 is a longitudinal sectional view similar to FIG. 48 but showing the mechanism fully charged and in position ready to dispense product.

FIG. 94 shows the mechanism fully charged and ready for a dispensing cycle, with the actuator 130 in its raised at-rest position, the piston 20 moved to enlarge the pump chamber 40 and draw a full charge of product into it, and the power spring 140 compressed and biasing the piston housing and piston in a direction to exert pressure on the product in the pump chamber.

Figure 95:
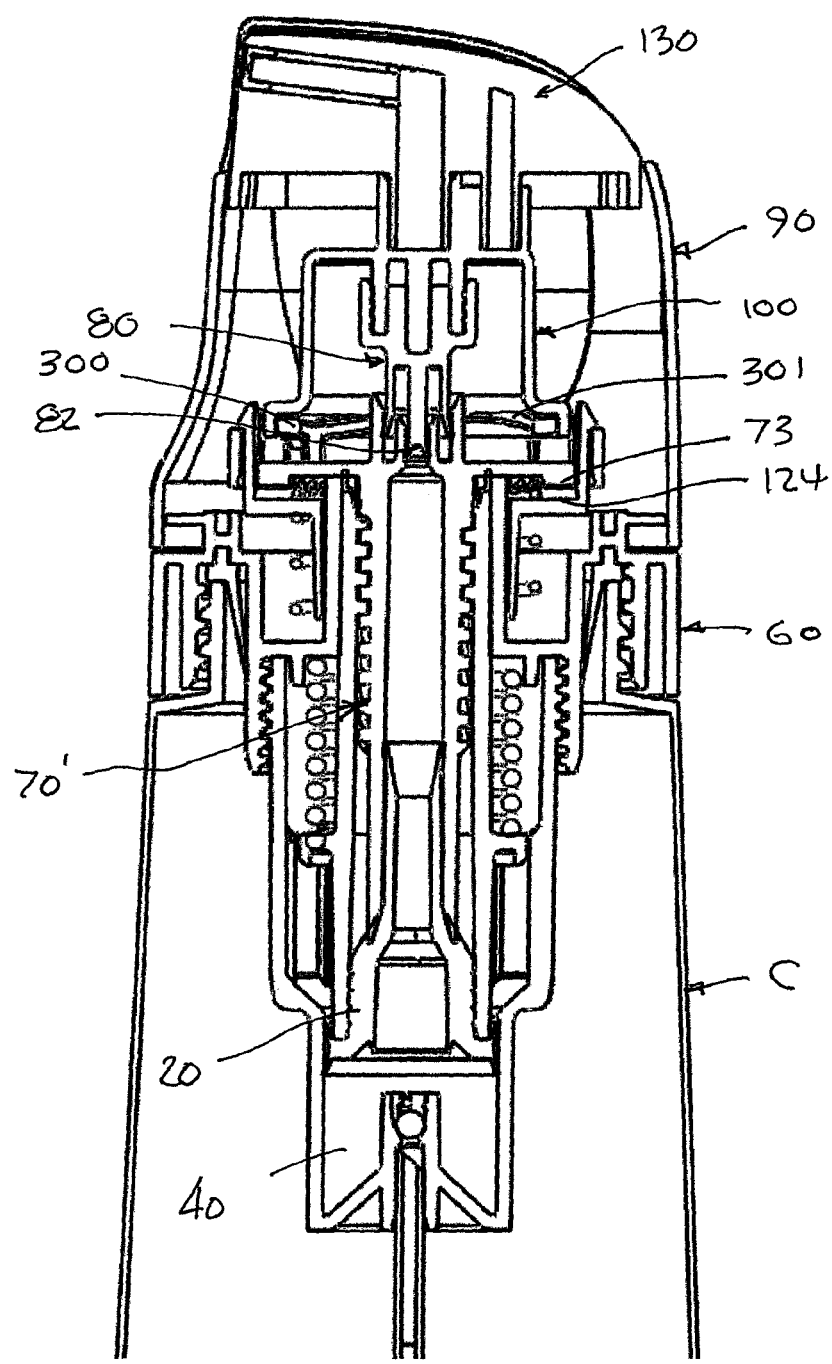
FIG. 95 is a view similar to FIG. 94 but showing the actuator partially depressed to move the clutch disc to disengage it from the drive screw.

FIG. 95 shows the actuator 130 partially depressed to disengage the gear teeth 124 on the clutch disc from the gear teeth 73 on the drive screw, while the stem valve 82 remains in a closed position.

Figure 96:
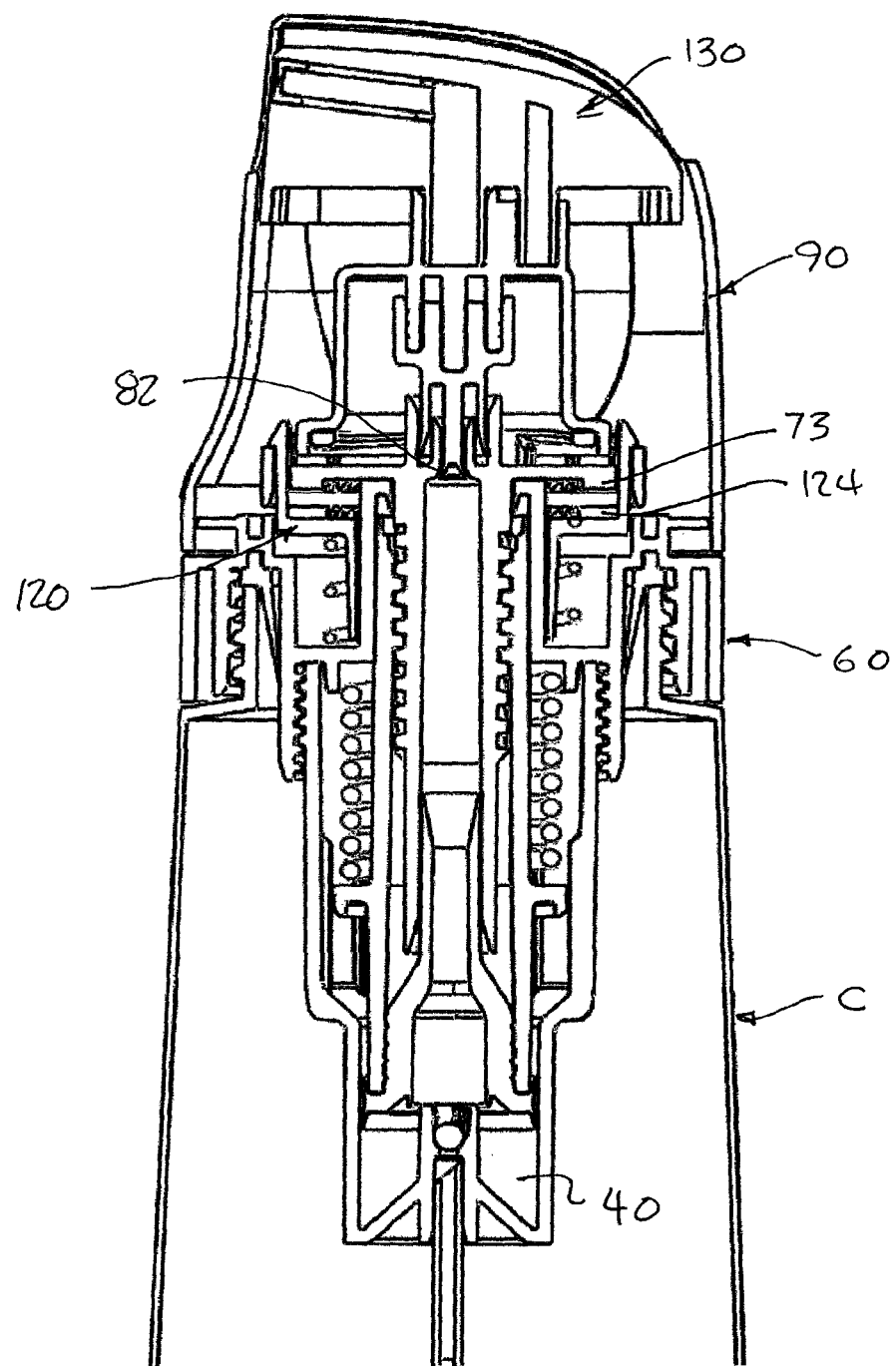
FIG. 96 is a view similar to FIG. 95 but showing the actuator fully depressed to open the stem valve to enable the power spring to move the piston to dispense product from the pump chamber.

FIG. 96 shows the actuator 130 fully depressed to open the stem valve 82 to enable the power spring 140 to move the piston 20 to dispense product from the pump chamber 40. In this state of the mechanism the clutch disc remains disengaged from the drive screw.

Figure 97:
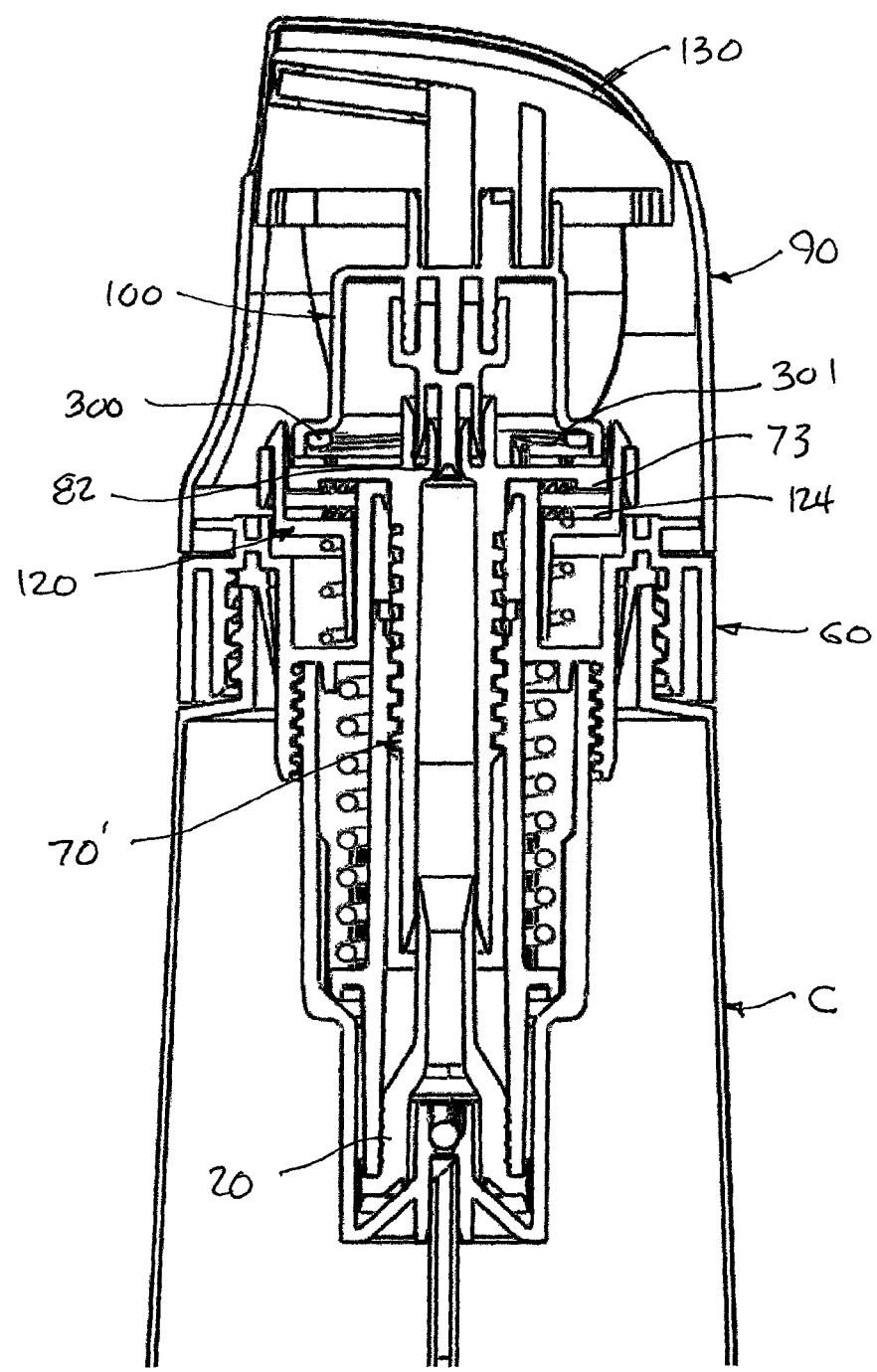
FIG. 97 is a view similar to FIG. 96 but showing the actuator returned to its at-rest position sufficiently to close the stem valve but with the clutch disc still disengaged from the drive screw.

In FIG. 97 the piston has forced all product from the pump chamber 40 and returned to its at-rest position. As shown in this figure the actuator remains fully depressed, the stem valve 82 remains in open position, and the clutch disc remains disengaged from the drive screw, with the actuator return springs 125 and 300, 301 compressed. When the actuator is released so that it can return to its at-rest position, the actuator return springs will first move the clutch disc and thus the actuator socket and stem valve sufficiently to close the stem valve but with the clutch disc still disengaged from the drive screw. This early closure of the stem valve blocks escape of product from the pump chamber and prevents the piston from moving toward its at-rest position before the clutch disc and drive screw are re-engaged, thereby ensuring that the actuator sleeve will not be caused to rotate by the piston during its return movement to its at-rest position. Full release of the actuator enables the drive screw to again engage with the clutch disc.

The common pump mechanism used in all embodiments of the disclosure requires only one turn or a partial turn of the actuator sleeve, which can be either left or right in design. Turning of the actuator sleeve causes the piston to move upwardly in the pump cylinder to draw product into the pump chamber and to store energy in the energy storage means. Of significance is the fact that depression of the actuator to open the stem valve and dispense product from the pump chamber also disengages the drive means between the piston and the actuator sleeve so that the piston can return to its at-rest position without causing rotation of the actuator sleeve.

Any one of several different types of energy storage means can be adapted to the common pump mechanism, including a spring mechanism as shown and described herein, or a pneumatic pressure mechanism or an elastic mechanism as illustrated and described in applicant's copending patent application Ser. No. 11/702,734, the disclosure of which is incorporated in full herein by reference. Each would produce the same results, but by being able to employ different energy storage means certain functional advantages can be obtained. For instance, a different energy storage means could be selected depending upon the range of pressure and force desired or needed to suit various viscosities of product.

With a pneumatic energy storage means, the initial at-rest pressure can easily be varied to suit particular requirements. With the spring loaded device, a new spring must be supplied to change the biasing force. Corresponding changes to the cylinder bore and piston diameter could also be made.

As can be seen, there is substantial flexibility provided by the dispensing system described herein without having to design and/or develop a completely new system for a given range of products. Also, the force mechanism may be employed with conventional mechanically operated pumps or triggers, reducing overall costs and eliminating the need to construct completely new systems. Although venting is required with the embodiments presented, airless systems may be employed. As can be understood, the present disclosure provides a convenience comparable to conventional aerosol systems. With the dispenser described herein there is no need to repeatedly pump an actuator and experience finger fatigue just to get short spurts of product. The embodiments described herein provide a duration spray and a convenience not available to date at an affordable price.

Since numerous modifications and combinations of the above embodiments can be arranged as shown and these embodiments will readily occur to those skilled in the art, it is not desired to limit the disclosure to the exact construction and process shown and described above. Accordingly, resort may be made to all suitable modifications and equivalents that fall within the scope of the disclosure as defined by the claims that follow. The words "comprise", "comprises", "comprising", "include(s)", and "including" when used in this specification and in the following claims are intended to specify the presence of stated features or steps, but they do not preclude the presence or addition of one or more other features, steps or groups thereof.

What is claimed is:

1. A method for dispensing a product from an interior volume of a container to which a power assembly is secured, the method comprising:
    (1) rotating an actuator sleeve of the power assembly in one direction 360° or less relative to the container to draw an amount of the product from the interior volume into a pump chamber and to pressurize the pump chamber;
    (2) temporarily depressing an actuator of the power assembly to open a valve that is in fluid communication with the pump chamber and that is normally biased to be in a closed position to dispense a portion of the product from the pump chamber through a nozzle for a duration of time during which the actuator is temporarily depressed;
    (3) releasing pressure on the actuator to permit the valve to return to the closed position before all of the product drawn in the pump chamber in step (1) is dispensed through the nozzle;
    (4) re-depressing and re-releasing pressure on the actuator sequentially one or more times until all of the product drawn in the pump chamber in step (1) is dispensed through the nozzle; and
    (5) repeating steps (1) through (4) to draw addition amounts of the product from the interior volume of the container and to dispense the additional amounts of the product through the nozzle;
    wherein, during the duration when the product is dispensed from the container, the power assembly does not rotate relative to the container, and
    wherein the power assembly is never rotated relative to the container in a direction opposite the one direction of rotation in step (1).

2. The method according to claim 1, steps (1) through (5) are repeated sequentially until all amounts of the product in the interior volume container that are capable of being drawn into the pump chamber in step (1) have been dispensed.

3. The method according to claim 1, wherein the container is a hand-held container, wherein the actuator sleeve is rotated by hand, and wherein the actuator is temporarily depressed by application of pressure by hand.

4. The method according to claim 1, wherein the product is dispensed from the nozzle in the form of a spray.

5. The method according to claim 1, wherein the power assembly is permanently secured to the container.

6. The method according to claim 1, wherein the actuator is not rotated at all relative to the container between steps (3) and (4).

7. The method according to claim 1, wherein in step (1), the actuator sleeve is rotated in the one direction relative to the container for only a partial portion of a full turn.

8. The method according to claim 1, wherein pressurization of the pump chamber in step (1) is effectuated using an energy storage device.

9. The method according to claim 8, wherein the energy storage device utilizes one or more springs, elastics or gases to exert pressure on a piston that pressurizes the pump chamber.

10. The method according to claim 9, wherein the energy storage device pre-stressed or pre-compressed to exert sufficient pressure on the piston that the product drawn in the pump chamber in step (1) is dispensable when the piston is near an at-rest position relative to a bottom of the pump chamber.

\* \* \* \* \*